United States Patent
Ojima

(10) Patent No.: US 6,187,916 B1
(45) Date of Patent: *Feb. 13, 2001

(54) PROCESS FOR THE PREPARATION OF TAXANE DERIVATIVES AND β-LACTAM INTERMEDIATES THEREFOR

(75) Inventor: Iwao Ojima, Stony Brook, NY (US)

(73) Assignee: Research Foundation of State University of New York, Stony Brook, NY (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/481,205

(22) Filed: Jun. 7, 1995

Related U.S. Application Data

(63) Continuation of application No. 08/383,610, filed on Feb. 2, 1995, now abandoned, which is a continuation of application No. 08/011,922, filed on Feb. 1, 1993, now abandoned.

(51) Int. Cl.[7] .................. C07D 205/08; C07D 305/14; C07F 7/18
(52) U.S. Cl. ............ 540/354; 540/357; 540/360; 549/510; 549/511
(58) Field of Search .................. 540/354, 357, 540/360

(56) References Cited

U.S. PATENT DOCUMENTS

| | | | |
|---|---|---|---|
| 5,015,744 | 5/1991 | Holton | 549/510 |
| 5,136,060 | * 8/1992 | Holton | 549/510 |
| 5,175,315 | * 12/1992 | Holton | 540/354 |
| 5,229,526 | * 7/1993 | Holton | 549/213 |

FOREIGN PATENT DOCUMENTS

| | | |
|---|---|---|
| 0400971 | 12/1990 | (EP). |
| 0428376 | 5/1991 | (EP). |

OTHER PUBLICATIONS

Ojima, J. Organic. Chemistry 56, 1681, 1991.*

(List continued on next page.)

*Primary Examiner*—Mark L. Berch
(74) *Attorney, Agent, or Firm*—Finnegan, Henderson, Farabow, Garrett & Dunner, L.L.P

(57) ABSTRACT

A process for the preparation of a taxane derivative of the formula

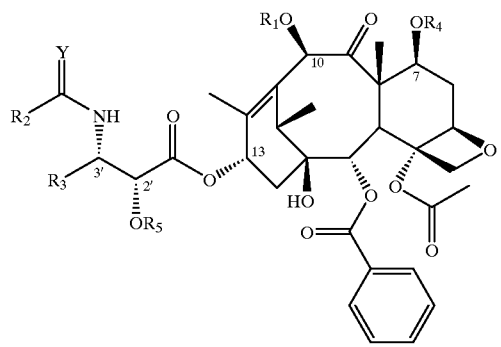

in which
$R_2$ represents an RO—, RS— or RR'N— in which R represents an unsubstituted or substituted straight chain or branched alkyl, alkenyl or alkynyl, or cycloalkyl, saturated heterocyclic, cycloalkenyl, unsaturated heterocyclic, aryl or heterocyclic aromatic; R' is a hydrogen or R defined above; R and R' can be connected to form together with the nitrogen a cyclic structure;
Y is oxygen or sulfur;
$R_3$ represents an unsubstituted or substituted straight chain or branched alkyl, alkenyl or alkynyl radical, an unsubstituted or substituted cycloalkyl, cycloalkenyl or an unsubstituted or substituted aryl;
which comprises reacting a β-lactam of the formula

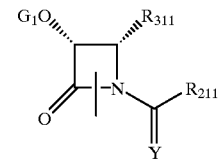

in which
$R_{311}$ represents a radical $R_3$ defined above or a protected $R_3$ whenever $R_3$ includes one or more active hydrogens; with a baccatin III derivative of the formula:

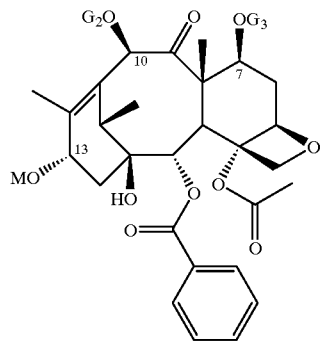

in which M is an alkali metal or alkaline earth metal atom (ion).

13 Claims, No Drawings

OTHER PUBLICATIONS

Denis, JACS 110, 5917, 1988.*
Denis, J. Organic. Chemistry 51, 46, 1986.*
Greene, "Protective Groups in Organic Synthesis" (Wiley & Sons), 504–505, 1999.*
Aoyama Tet. Letters 24, 1169 (1983).*
"Condensed Chemical Dictionary" (10th Edition, 1983) p. 758.*
Ojima, Tet. 48, 6985 (1992).*
Ojima, Bioinorganic & Nuclear Letters 3 2479 (1993).*
Commercon, Tet. Letters 33, 5185 (1992).*
Bourzat, Tet. Letters 34, 6049 (1993).*
"Organic Chemistry" (Morrison & Boyd) $5^{th}$ Edition, 1990 p. 435.

* cited by examiner

PROCESS FOR THE PREPARATION OF TAXANE DERIVATIVES AND β-LACTAM INTERMEDIATES THEREFOR

This is a continuation of application Ser. No. 08/383,610 filed Feb. 2, 1995, abandoned, which is a continuation of application Ser. No. 08/011,922 filed Feb. 1, 1993 abandoned.

FIELD OF THE INVENTION

The present invention relates to a process for the preparation of taxoid(s) including TAXOTÈRE and its analogs and the β-lactam intermediates useful in this process.

BACKGROUND OF THE INVENTION

Taxol (I) is a complex diterpene which is currently considered the most exciting lead in cancer chemotherapy. Taxol possesses high cytotoxicity and strong antitumor activity against different cancers which have not been effectively treated by existing antitumor drugs. For example, taxol is currently in phase III clinical trial for advanced ovarian cancer, phase II for breast cancer, and phase I for lung cancers, colon cancer and acute leukemia.

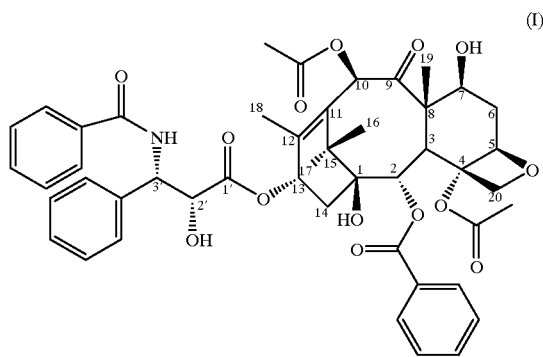

Although taxol is an extremely important "lead" in cancer chemotherapy, taxol has a problem with solubility in aqueous media, which may impose some serious limitation in its use. It is common for improved drugs to be derived from naturally occurring lead compounds. In fact, French researchers, Potierf Guéritte-Voegelein, Guénard et al. have discovered that a modification of the C-13 side chain of taxol brought about a new anticancer agent which seems to have antitumor activity superior to taxol with better bioavailability. This synthetic compound was named "TAXOTÈRE (II)", which has t-butoxycarbonyl instead of benzoyl on the amino group of (2R,3S)-phenylisoserine moiety at the C-13 position and a hydroxyl group instead of acetoxy group at C-10. [Colin, M. et al. Eur. Pat. Appl. EP253,738 (1988)]. Taxotére is currently in phase II clinical trial in both United States and Europe. TAXOTÈRE has been synthesized by a semisynthetic process, including a coupling of N-tert-butoxycarbonyl-(2R,3S)-3-phenylisoserine with 10-deacetylbaccatin III with proper protecting groups. (Denis, J. -N. recently reported (Commerçon, A. et al., Tetrahedron Letters, 1992, 33 5185).

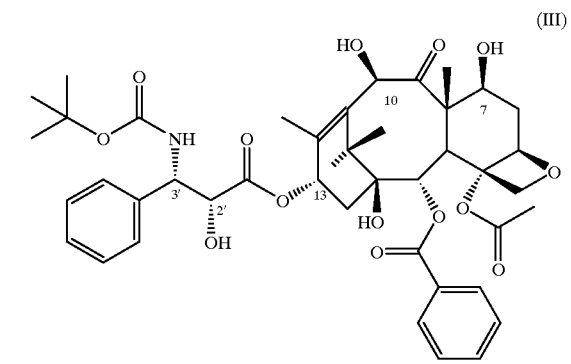

It is known that the C-13 side chain of taxol, i.e., N-benzoyl-(2R,3S)-3-phenylisoserine (III) moiety, is crucial for the strong antitumor activity of taxol. (Senilh et al., C. R. Séances Acad. Sci. Ser. 2 1984, 299, 1039; Guéritte-Voegelein et al., Tetrahedron, 1986, 42, 4451, and Mangatal et al., Tetrahedron, 1989, 45, 4177; Guéritte-Voegelein et al. J. Med. Chem. 1991, 34, 992; and Swindell et al., J. Med. Chem. 1992, 35, 145; Mathew, A. E. Et al., J. Med. Chem. 1992, 35, 145). Moreover, some modification of the C-13 side chain can provide a new series of taxol analogs which may have higher potency, better bioavailability and less unwanted toxicity, as exemplified by the discovery of TAXOTÈRE (II).

Accordingly, the development of an efficient method which can be applied to various analogs of taxol and TAXOTÈRE and analogs thereof, i.e., a method having flexibility and wide applicability, is extremely important and of current demand. It has been shown that such a new and efficient method with flexibility can be developed by using enantiomerically pure β-lactams as key-intermediates [Ojima, I. et al., J. Org. Chem., 1991, 56, 1681; Ojima et al., Tetrahedron, 1992, 48, 6985; Holton, R. A., Eur. Patent Appl. EP 400,971 (1990)].

Lithium chiral ester enolate-imine cyclocondensation strategy has been applied to the asymmetric synthesis of the side chain of taxol via a (3R,4S)-3-hydroxy-4-phenylazetidin-2-one (IV) as the key-intermediate. (Ojima, I. et al., J. Org. Chem., 1991, 56, 1681; Ojima et al., Tetrahedron, 1992, 48, 6985)

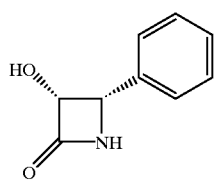

(IV)

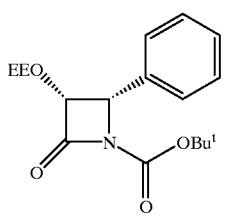

(VII)

Based on this protocol, the side chain can be obtained in 3 steps in high yield with virtually 100% e.e. (Ojima, I. et al. J. Org. Chem. 1991 56, 1681). Recently, it was found that 1-benzoyl-(3R, 4S)-3-(1-ethoxyethoxy)-4-phenylazetidin-2-one (V), readily derived from the hydroxy-β-lactam (IV), served as the key-intermediate for the synthesis of taxol [Holton, R. A. Eur. Pat. Appl. EP 400,971 (1990)]. Therefore, this β-lactam intermediate serves as the key-intermediate for both coupling methods.

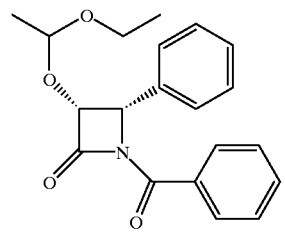

(V)

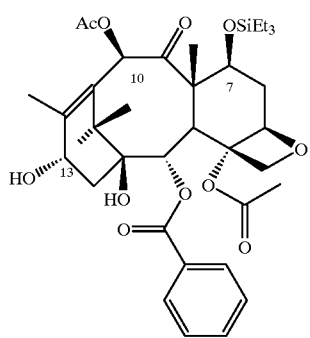

(VI)

7-TES-baccatin III

In the published European application to Holton (hereinafter Holton), the β-lactam intermediate (V) was obtained through tedious optical resolution of the racemic cis-3-hydroxy-β-lactam. According to Holton's procedure, the coupling of the β-lactam (V) with 7-triethylsilylbaccatin III (VI) (7-TES-baccatin III) proceeds at 25° C. in the presence of dimethylaminopyridine (DMAP) and pyridine for 12 hours to give protected taxol in 92% yield, which was deprotected with 0.5% hydrochloric acid in ethanol at 0° C. to afford taxol in ca. 90% yield.

However, the Holton procedure did not work at all when 1-tert-butoxycarbonyl-(3R, 4S)-3-(1-ethoxyethoxy)-4-phenylazetidin-2-one (VII) was used for the attempted synthesis of TAXOTÈRE (II) by the present inventors.

It is believed that this may be due to the lack of reactivity of the 1-tert-butoxycarbonyl-β-lactam (VII) toward the C-13 hydroxyl group of a protected baccatin III (VI or VIII) under the conditions used by Holton. The lack of reactivity may be ascribed to the substantially weaker electron-withdrawing ability of tert-butoxycarbonyl group than that of benzoyl group.

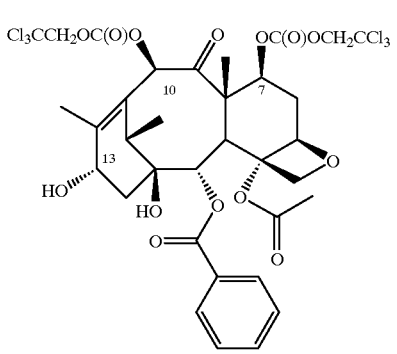

(VIII)

7, 10-di-Troc-10-deacetylbaccatin III

Therefore, it was an objective of the present invention to develop a new method which can achieve the coupling of the 1-tert-butoxycarbonyl-β-lactam (VII) with the protected baccatin III (VIII) for the synthesis of TAXOTÈRE (II).

All of the references cited above and any reference which may be mentioned hereinbelow are expressly incorporated into the present diclosure.

It is an object of the present invention to provide new β-lactams useful in the syntheses of TAXOTÈRE (II) and analogs thereof.

It is further object of the present invention to provide a new coupling method for the syntheses of TAXOTÈRE (II) and analogs thereof.

SUMMARY OF THE INVENTION

A β-lactam of the formula (IX)

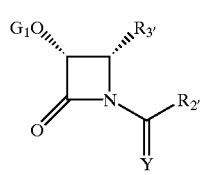

(IX)

in which $R_{2'}$ represents an RO—, RS— or RR'N— in which R represents an unsubstituted or substituted straight chain or branched alkyl, alkenyl or alkynyl, cycloalkyl, heterocycloalkyl, cycloalkenyl, heterocycloalkenyl, carbocyclic aryl or heteroaryl, wherein substituents bearing one or more active hydrogens such as hydroxyl, amino, mercapto and carboxyl groups are protected; R' is a hydrogen or R as defined above; R and R' can be connected to form a cyclic structure; Examples of $R_{2'}$ include methoxy, ethoxy, isopropoxy, tert-butoxy, neopentyloxy, cyclohexyloxy, allyloxy, propargyloxy, adamantyloxy, phenyoxy, 4-methoxyphenoxy, 2-fluorophenoxy, 4-methoxycarbonylphenoxy, methylthio, ethylthio, isopropylthio, tert-butylthio, neopentylthio, cyclohexylthio, phenylthio, 3,4-dimethoxyphenylthio, methylamino, ethylamino, isopropylamino, tert-butylamino, neopentylamino, cyclohexylamino, dimethylamino, pyrrolidino, piperidino and morpholino group.

$R_{2'}$ may also represent a radical RO—, RS— or RR'N— in which R represents a straight chain or branched alkyl radical containing 1 to 20 carbon atoms, a straight chain or branched alkenyl radical containing 2 to 20 carbon atoms, a straight chain or branched alkynyl radical containing 2 to 10 carbon atoms, a cycloakyl radical containing 3 to 10 carbon atoms, a heterocyclic radical containing 3 to 10 carbon atoms, a cycloalkenyl radical containing 3 to 10 carbon atoms, a heterocycloalkenyl radical containing 3 to 10 carbon atoms, a polycloaklyl radical containing 6 to 20 carbon atoms, an aryl radical containing 6 to 20 carbon atoms, or a heteroaryl radical containing 3 to 15 carbon atoms.

$R_{2'}$ may also represent a radical RO—, RS— or RR'N— in which R represents an unsubstituted or substituted alkyl radical selected from methyl, ethyl, propyl, isopropyl, butyl, isobutyl, tert-butyl, pentyl, isopentyl, neopentyl, hexyl, isohexyl, (2-methylpentyl), heptyl, isoheptyl (2-methylhexyl), octyl, isooctyl (2-methylheptyl); a 9-fluoroenylmethyl radical; a cycloalkyl radical selected from cyclopropyl, cyclobutyl, cyclopentyl, cyclohexyl, cycloheptyl,cyclooctyl, and adamantyl; an alkenyl radicak selected from vinyl and allyl; an aryl radical selected from phenyl and naphthyl; a benzyl radical; a hetrocyclic aromatic radical selected from furyl, pyrrolyl, and pyridyl; a cycloakenyl radical selected from cyclohexenyl, and cycloheptenyl; a saturated heterocyclic radical selected from oxiranyl, tetrahydofuryl, prrolidinyl, piperidinyl, tetrahydropyranyl; or an unsaturated heterocyclic radical selected from dihydrofuryl, dihydropyrrolyl, dihydropyranyl, or dihydropyrridyl. The cyclic RR'N— radical may be aziridino, azetidino, pyrrolidino, piperidino, or morpholino.

$R_{3'}$ represents an unsubstituted or substituted straight chain or branched alkyl, alkenyl or alkynyl radical, an unsubstituted or substituted cycloalkyl, or cycloalkenyl radical, an unsubstituted or substituted aryl radical wherein substituents bearing one or more active hydrogens such as hydroxyl, amino, mercapto and carboxyl groups are protected; Examples of $R_3'$ include phenyl, 4-methoxylphenyl, tolyl, 3,4-dimethoxylphenyl, 4-fluorophenyl, 4-trifluoromethylphenyl, 4-chlorophenyl, 4-bromophenyl, naphthyl, cyclohexyl, cyclohexylmethyl, 2-phenylethenyl, 2-phenylethyl, benzyl, neopentyl, tert-butyl, isobutyl, isopropyl, allyl and propargyl;

$R_{3'}$ may also represent a straight chain or branched alkyl radical containing 1 to 10 carbon atoms, a straight chain or branched alkenyl radical containing 2 to 10 carbon atoms, a straight chain or branched alknyl radical containing 2 to 10 carbon atoms, a cycloalkyl radical containing 3 to 10 carbon atoms, a cycloalkenyl radical containing 3 to 10 carbon atoms, a polycycloalkyl radical containing 6 to 20 carbon atoms, or an aryl radical containing 6 to 20 carbon atoms.

$R_{3'}$ may further represent an unsubstituted or substituted alkyl radical selected from methyl, ethyl, propyl, isopropyl, butyl, isobutyl, tert-butyl, pentyl, isopentyl, neopentyl, hexyl, isohexyl, (2-methypentyl), heptyl, isoheptyl, (2-methylhexyl), octyl, isooctyl (2-methylheptyl); a 9-fluoroenylmethyl radical; a cycloalkyl radical selected from cyclopropyl, cyclobutyl, cyclopentyl, cyclohexyl, cycloheptyl, cyclootyl, and adamantyl; a cyclohexylmethyl radical; an alkenyl radical selected from vinyl and allyl; an alkynyl radical selected from ethynyl and propargyl; an aryl radical selected from phenyl, tolyl, and naphthyl; a benzyl radical; a cyclohexylethyl radical; a phenylethyl radical; 2-phenylethenyl radical or a cycloalkenyl radical selected from cyclohexenyl, and cycloheptenyl.

The substituents for R,$R_{2'}$ and $R_{3'}$ also include one or more halogen atoms or hydroxyl, alkoxy, aryloxy, heterocyclic aryloxy, amino, alkylamino, dialkylamino, mercapo, alkylthio, arylthio, heterocyclic arylthio, cyano, carboxyl, alkoxycarbonyl, aryloxycarbonyl, or heterocyclic aryloxcarbonyl radicals. Preferably, the alkyl portion of the alkoxycarbonyl radical contains 1 to 15 carbon atoms, the aryl portion of the aryloxycarbonyl radical contains 6 to 20 carbon atoms, and the heterocyclic aryl portion of the heterocyclic aryloxycarbonyl radical contains 3 to 15 carbon atoms.

$G_1$ represents a hydrogen or a hydroxyl proteting group such as methoxymethyl (MOM), methoxylethyl (MEM), 1-ethoxyethyl (EE) benzylbxymethyl, (β-trimethylsilylethoxyl)methyl, tetrahydropyranyl, 2,2,2-trichloroethoxylcarbonyl (Troc), tert-butoxycarbonyl (t-BOC), 9-fluorenylmethoxycarbonyl (Fmoc), 2,2,2-trichloroethoxymethyl, trimethylsilyl, triethylsilyl, dimethylethylsilyl, dimethyl(t-butyl)silyl, diethylmethylsilyl, dimethylphenylsilyl and diphenylmethylsilyl;

Y is oxygen or sulfur.

The present inventor investigated the β-lactam coupling reaction with protected Baccatin III in detail and found that the coupling could be achieved by increasing the nucleophilicity of the 13-hydroxyl group of a protected baccatin III (VI or VIII) through transformation of the hydroxyl group to the corresponding metal alkoxide. Such a C-13 metal alkoxide of. a baccatin III was readily generated by reacting the baccatin III (VI or VIII) with an alkali or alkaline earth metal base. This finding is the basis of the present invention. The method of the present invention not only enables the coupling of the β-lactam (VII) and its derivatives and analogs with a protected baccatin III, but also requires only a stoichiometric amount of the β-lactams. The latter makes a sharp contrast with the Holton procedure for taxol synthesis which needs 5–6 equivalents of the more reactive β-lactam (V). Moreover, the coupling reactions of the present invention proceed very smoothly and complete typically within 30 minutes at −30°–0° C.

The present invention also relates to a process for the preparation of taxane derivatives of the formula (X)

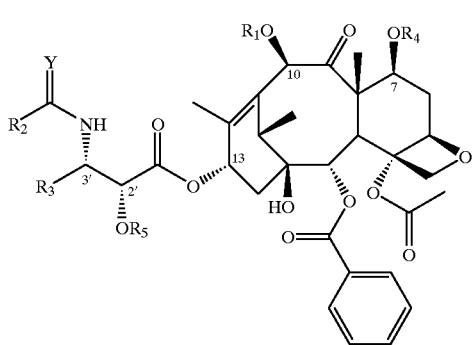

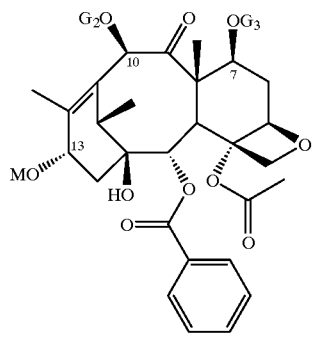

in which

R₁ represents a hydrogen atom or an acyl or an alkyl or an alkenyl or an alkynyl or carbocyclic aryl or a heteroaryl radical or a hydroxyl protecting group ($G_1$ defined above);

$R_2$ represents an RO—, RS— or RR'N— in which R represents an unsubstituted or substituted straight chain or branched alkyl, alkenyl or alkynyl, cycloalkyl, heterocycloalkyl, cycloalkenyl, heterocycloalkenyl, carbocyclic aryl or heteroaryl; R' is a hydrogen or R as defined above; R and R' can be connected to form a cyclic structure;

Y is oxygen or sulfur;

$R_3$ represents an unsubstituted or substituted straight chain or branched alkyl, alkenyl radical, an unsubstituted or substituted cycloalkyl, cycloalkenyl radical or an unsubstituted or substituted carbocyclic aryl radical;

$R_4$ represents a hydrogen or an acyl radical or an unsubstituted or substituted straight chain or branched alkyl, alkenyl or alkynyl radical, an unsubstituted or substituted cycloalkyl, heterocycloalkyl, cycloalkenyl or heterocycloalkenyl radical, an unsubstituted or substituted carbocyclic aryl or heteroaryl radical, or a hydroxyl group protecting group ($G_1$ defined above);

$R_5$ represents a hydrogen or an acyl radical or an unsubstituted or substituted straight chain or branched alkyl, alkenyl or alkynyl radical, an unsubstituted or substituted cycloalkyl, heterocycloalkyl, cycloalkenyl or heterocycloalkenyl radical, an unsubstituted or substituted carboyclic aryl or heteroaryl radical, or a hydroxyl protecting group ($G_1$ defined above);

which comprises condensing a β-lactam of the formula

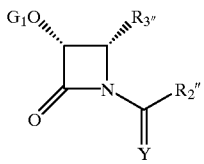

in which

Y and $G_1$ are defined above;

$R_{2''}$ represents a radical $R_2$ as defined above or a protected $R_2$ whenever $R_2$ includes one or more active hydrogens such as hydroxyl, amino, mercapto and carboxyl groups;

$R_{3''}$ represents a radical as $R_3$ defined above or a protected $R_3$ whenever $R_3$ includes one or more active hydrogens such as hydroxyl, amino, mercapto and carboxyl groups; with abaccatin III derivative of the formula:

in which

M is an alkali metal or alkaline earth metal atom (ion);

$G_2$ represents a hydroxyl protecting group ($G_1$ defined above) or an acyl radical or an unsubstituted or substituted straight chain or branched alkyl, alkenyl or alkynyl radical, an unsubstituted or substituted cycloalkyl, heteroycloalkyl, cycloalkenyl or heterocycloalkenyl radical, an unsubstituted or substituted carbocyclic aryl or heteroaryl radical;

$G_3$ represents a hydroxyl group protecting group ($G_1$ defined above) or an acyl radical or an unsubstituted or Substituted straight chain or branched alkyl, alkenyl or alkynyl radical, an unsubstituted or substituted cycloalkyl, heterocycloalkyl, cyloalkenyl or heterocycloalkenyl radical, an unsubstituted or substituted carbocyclic aryl or heteroaryl radical.

DETAILED DESCRIPTION OF THE INVENTION

The new β-lactams of the formula (IX) hereinabove are synthesized by modifying the β-lactams of the formula (XI)

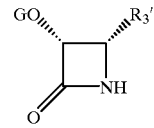

wherein G is a hydroxyl protecting group such as triisopropylsilyl (TIPS) and dimethyl(tert-butyl)silyl (TBDMS), and $R_3'$ has been defined hereinabove.

The β-lactams (XI) are readily prepared by using the chiral enolate-imine cyclocondensation method which has been developed in the present inventors laboratory as shown in Scheme 1 (Ojima, I. et al., Tetrahedron, 1992, 48, 6985; Ojima, I. et al., J. Org. Chem. 1991, 56, 1681). In this preparation the β-lactams (XI) with extremely high enantiomeric purities are obtained in high yields. In Scheme 1, R* is a chiral auxiliary moiety which is (−)-trans-2-phenyl-1-cyclohexyl, TMS is a trimethylsilyl radical, and base is lithium diisopropylamide or lithium hexamethyldisilazide; G and $R_3'$ have been defined hereinabove.

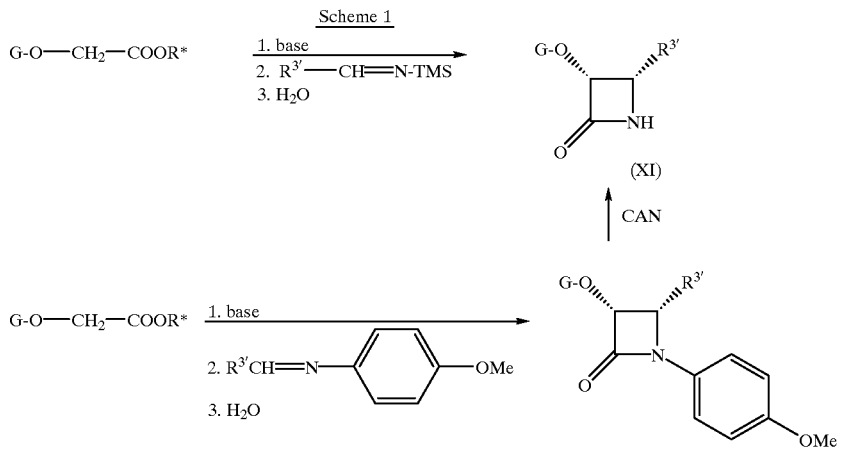

The β-lactams (XI) are converted to the 3-hydroxy-β-lactams (XII), followed by protection with ethoxyethyl group (EE) to give the β-lactams (XIII). The β-lactams (XIII) are reacted with chloroformates or formic anhydrides or thiochloroformates or thioformic anhydrides in the presence of a base to yield the β-lactams (XIV) (or thioanalogs thereof) which are used for the Coupling with protected 10-deacetylbaccatin III to produce TAXOTÈRE and its analogs. The β-lactams (XIV) are deprotected under weakly acidic conditions to afford the β-lactams (XV) which can serve as very useful intermediates to the β-lactams (XVI) bearing a variety of protecting groups ($G_1$) at the C-3 position of β-lactam skeleton. The β-lactams (XVI) can also be used for the coupling with a protected 10-deacetylbaccatin III to produce Taxotére and its analogs after deprotection.

In a similar manner, the β-lactams (XVII) are prepared by reacting the β-lactams (XIII) with isocyanates or isothiocyanates in the presence of a base which can be used for the production of other potent anticancer agents of formula (X) in which $R_3$ represents RR'N—. The β-lactams (XVII) are deprotected under weakly acidic conditions to give the β-lactams (XVIII) which can serve as very useful intermediates to a variety of protected 3-hydroxyl-β-lactams (XIX). The β-lactams (XVII and XIX) can also be used for the coupling with a protected 10-deacetylbaccatin III to yield a compound of formula (X) in which $R_2$ represents RR'N— after deprotection.

In a manner similar to that described above, the β-lactams (XX) are prepared by reacting the β-lactams (XIII) with N,N-disubstituted carbamoyl halides in the presence of a base. The β-lactams (XX) are deprotected under weakly acidic conditions to give the 3-hydroxy-β-lactams (XXI), which can serve as very useful intermediates to various protected 3-hydroxy-β-lactams (XXII). The β-lactams (XX and XXII) can readily be used for the coupling with a protected baccatin III to afford a compound of formula (X) after deprotection.

The transformations described above are illustrated in Scheme 2. In Scheme 2, X represents a leaving group such as fluoride, chloride, bromide, iodide, tosylate, mesylate and trifluoromesylate. $G_1$ represents a group protecting the hydroxyl function selected from methoxylmethyl (MOM), methoxyethyl (MEM), 1-ethoxyethyl (EE), benzyloxymethyl, (β-trimethylsilylethoxyl) methyl, tetrahydropyranyl, 2,2,2-trichloroethoxylcarbonyl (Troc), benzyloxycarbonyl (CBZ), tertbutoxycarbonyl (t-BOC), 9-fluorenyl methoxycarbonyl (Fmoc), 2,2,2-trichloroethoxymethyl, trimethyl silyl, dimethyl(t-butyl) silyl, diethylmethylsilyl, dimethyl phenylsilyl and diphenylmethylsilyl, acetyl, chloroacetyl, dichloroacetyl, trichloroacetyl and trifluoroacetyl. $R^{2'}$, $R^{3'}$, R, and R' are defined hereinabove.

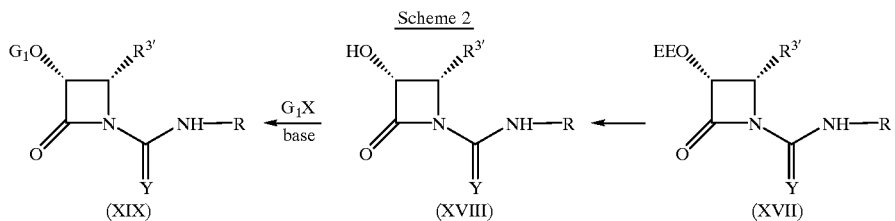

-continued
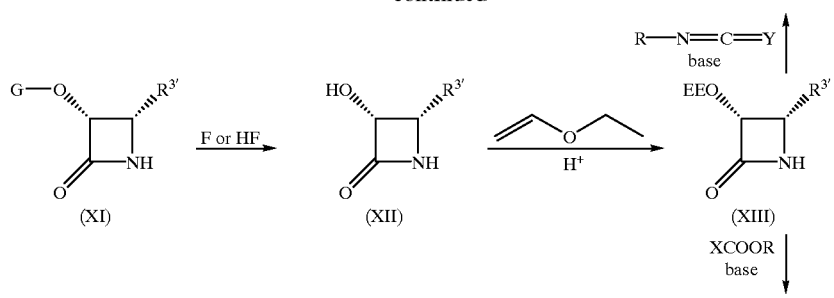
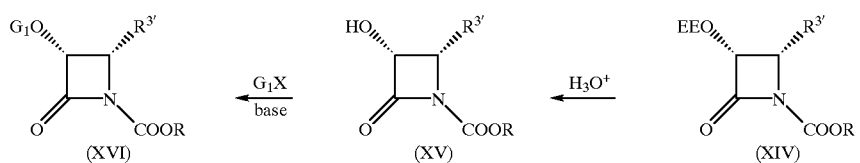
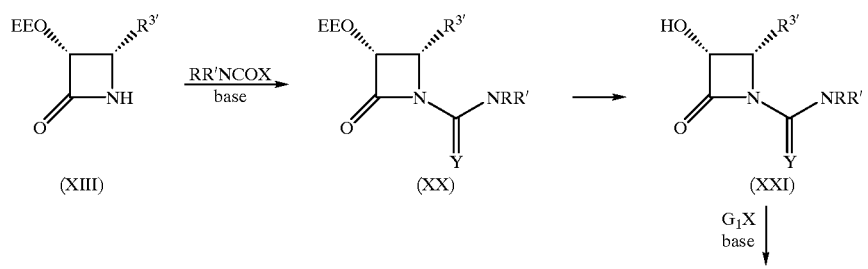
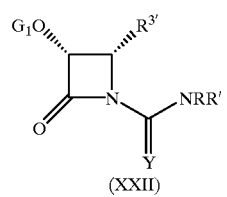

The β-lactams (XIV) and (XVI) are readily used for the coupling with protected baccatin IIIs in the presence of base, followed by deprotection to give TAXOTERE and its analogs in high yields (Scheme 3). In a similar manner, the β-lactams (XVII and XIX; with protection of —NH— moiety) and the β-lactams (XX and XXII) can be used for the coupling with protected baccatin IIIs, followed by deprotection to give a compound of formula (X) in which $R_2$ represents $RR^1N$— (Scheme 3).

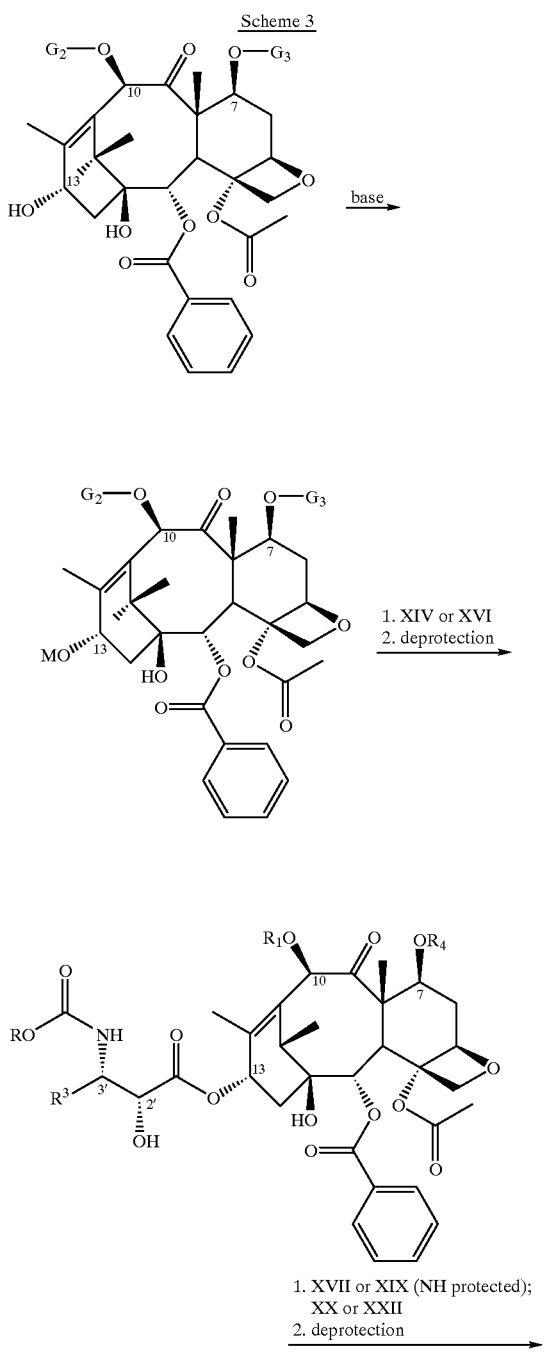

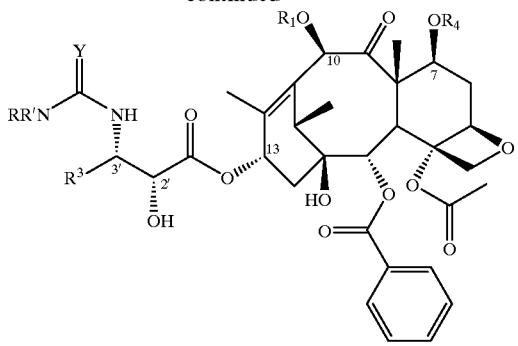

-continued $G_2$ and $G_3$ represents an hydroxyl protecting group or an acyl radical or an unsubstituted or substituted straight chain or branched alkyl, alkenyl radical, an unsubstituted or substituted cycloalkyl, heterocycloalkyl, cycloalkenyl or heterocycloalkenyl radical, an unsubstituted or substituted carbocyclic aryl or heteroaryl radical.

When $G_2$ and $G_3$ are hydroxyl protecting groups [$G_1$ defined above and 1-ethoxyethoxyl (EE)], these protecting groups can be attached to the hydroxyl groups of 10-deacetylbaccatin III and its analogs by methods which are generally known to those skilled in the art.

The coupling reaction of the protected baccatin III and the β-lactam is carried out via an alkali metal or alkaline earth metal alkoxide of the protected baccatin III at the C-13 hydroxyl group. The alkoxide can readily be generated by reacting the protected baccatin III with an alkali metal or alkaline earth metal base such as sodium hexamethyldisilazide, potassium hexamethyldisilazide, lithium hexamethyldisilazide, sodium diisopropylamide, potassium diisopropylamide, lithium diisopropylamide, sodium hydride, potassium hydride, lithium hydride, calcium hydride, magnesium hydride, in a dry nonprotic organic solvent such as tetrahydrofuran (THF), dioxane, ether, dimethoxyethane (DME), diglyme, dimethylformamide (DMF), mixtures of these solvents with hexane, toluene, and xylene, in a preferred temperature range from about −100° C. to about 50° C., more preferably at about −78° C. to about 25° C. This reaction is preferably carried out under inert atmosphere such as nitrogen and argon. The amount of the base used for the reaction is preferably approximately equivalent to the amount of the protected baccatin III when soluble bases such as sodium hexamethyldisilazide, potassium hexamethyldisilazide, lithium hexamethyldisilazide, sodium diisopropylamide, potassium diisopropylamide, lithium diisopropylamide are used. The use of a slight excess of the base does not adversely affect the reaction. When heterogeneous bases such as sodium hydride and potassium hydride are used, 5–10 equivalents of the base (to the amount of the protected baccatin III) is preferably employed.

The coupling reaction of the metal alkoxide of the protected baccatin III thus generated with the β-lactam is typically carried out by adding the solution of the β-lactam in a dry organic solvent exemplified above in a preferred temperature range from about −100° C. to 50° C., more preferably at about −35° C. to 25° C. The mixture of reactants is stirred for 15 minutes to 24 hours and the progress and the completion of the reaction is monitored by thin layer chromatography (TLC), for example. When the limiting reactant is completely consumed, the reaction is quenched by addition of a brine. The crude reaction mixture is worked up using the standard isolation procedures which are generally known to those skilled in the art to give the corresponding protected taxoid. The proportion of the β-lactam and the protected baccatin III is in a range from 2:1 to 1:2, more preferably approximately 1:1 for purposes of economy and efficiency, but the ratio is not critical for the reaction.

The protecting groups, EE, $G_1$, $G_2$ and $G_3$, can then be removed by using the standard procedures which are generally known to those skilled in the art to give the desired taxane derivatives. For example, EE and triethylsilyl groups can be removed with 0.5 N HCl at room temperature for 36 h, and Troc group can be removed with zinc and acetic acid in methanol at 60° C. for 1 hour without disturbing the other functional groups and the skeleton of the taxoid.

The following non-limiting examples are illustrative of the present invention. It should be noted that various changes would be made in the above examples and processes therein without departing from the scope of the present invention. For this reason, it is intended that the illustrative embodiments of the present application should be interpreted as being illustrative and not limiting in any sense.

EXAMPLES 1–2

(3R,4S)-3-Triisopropylsilyloxy-4-phenyl-2-azetidinone (1a): To a solution of 645 mL (4.6 mmol) of diisopropylamine in 10 mL of THF, was added 1.85 mL (4.6 mmol, 2.5M) of n-BuLi at 0° C. The solution was stirred 1 h at 0° C. followed by the addition of 1.5 g (3.8 mmol) of (−) TIPS ester in 15 mL of THF over a 1 h period (using a cannula) at −78° C. The reaction was stirred 2 h at this temperature followed by the addition of 817 mg (4.6 mmol) of N-TMS benzaldimine in 15 mL of THF over a 2 h period at −95° C. The reaction was stirred overnight at this temperature and allowed to slowly warm up at room temperature. The reaction was quenched by addition of sat. NH$_4$Cl. The aqueous layer was extracted with ether. The organic layer was washed with 3% HCl and brine, dried over MgSO$_4$ and concentrated. The crude oil was purified by chromatography on silica gel using 1:5 EtAcO/hexanes to give 1.03 g (84%) of β-lactam as a white solid: Mp 76–77° C.; $[\alpha]D^{20}$ +52.7° (c 1.00, CHCl$_3$); $^1$H NMR (300 MHz, CDCl$_3$) δ 0.86–0.93 (m, 21H), 4.81 (d, J=4.7 Hz, 1H), 5.17 (dd, J=4.7, 2.6 Hz, 1H), 6.18 (bs, 1H), 7.17–7.35 (m, 5H); $^{13}$C NMR (75 MHz, CDCl$_3$) δ 11.8, 17.4, 17.5, 59.6, 79.9, 127.9, 128.0, 128.1, 136.4, 170.0; IR (KBr) 3234, 2946–2866, 1760, 1458 cm$^{-1}$. Anal. Calcd for C$_{18}$H$_{29}$NO$_2$Si: C$_{67.66}$%, H 9.15%, N 4.38%. Found: C$_{67.64}$%, H 9.25%, N 4.44%.

In the same manner, β-lactam 1b was obtained in good yield.

(3R,4S)-3-Triisopropylsilyloxy-4-(2-phenylethenyl)-2-azetidinone (1b): 72%; colorless liquid; $_1$H NMR (300 MHz, CDCl$_3$) δ 0.98–1.02 (m, 21H), 4.36 (dd, J=4.6, 8.3 Hz, 1H), 5.09 (dd, J=2.3, 4.6 Hz, 1H), 6.29 (dd, J=8.3, 16.0 Hz, 1H), 6.59 (d, J=16.0 Hz, 1H), 6.83, (bs, 1H), 7.23–7.39 (m, 5H); NMR (75 MHz, CDCl$_3$) δ 11.79, 17.61, 17.66, 58.34, 79.86, 126.05, 126.45, 127.90, 128.56, 134.41, 136.30, 169.69; IR (neat) 3262, 3032, 2944, 2865, 1748, 1672, 1623 cm$^{-1}$. Anal. Calcd for C$_{20}$H$_{31}$NO$_2$Si: C, 69.52; H, 9.04; N, 4.05. Found: C, 69.75; H, 9.02; N, 3.89.

EXAMPLES 3–4

To a solution of 2.51 mmol of diisopropylamine in 15 mL of THF was added 2.51 mL of n-butyllithium (2.5M in THF) at −10° C. After 30 min, the llithium diisoipropylamide (LDA) was generated and the solution was cooled to −95° C. A solution of 2.17 mmol of chiral ester in 5 mL of THF was added. After 1 hr, a solution of 2.5 mmol of the appropriate imine in 3mL of THF was added. The mixture was stirred at −95° C. overnight, and the progress of the reaction was monitored by TLC or $^1$H NMR. The reaction was quenched with sat. NH$_4$Cl and THF was removed using a rotary evaporator. Ether (10 mL) was added and the aqueous layer was extracted with ether (10 mL×3). Drying and removal of the solvent gave the crude product which was purified by silica gel column chromatography (hexane/ethyl acetate= 10:1) to afford the corresponding pure β-lactam. The enantiomeric excess was determined by HPLC using a CHIRAL-CEL OD column using n-hexane/i-PrOH (90/10) as the eluent. (3R, 4S)-4-(2-Methylpropyl)-1-(4-methoxyphenyl)-3-triisopropylsilyloxy-2-azetidinone (2a): 87%; pale yellow solid; mp 59–60° C.; $[\alpha]D^{20}$ +60.46° (c 1.26, CHCl$_3$); $^1$H NMR (300 MHz, CDCl$_3$) δ 0.96 (d, J=6.4 Hz, 3H), 1.03 (d, J=6.4 Hz, 3H), 1.10–1.30 (m, 21H), 1.60–1.68 (m, 1H), 1.70–1.92 (m, 2H), 3.75 (s, 3H), 4.16–4.22 (m, 1H), 5.06 (d, J=5.1 Hz, 1H), 6.86 (d, J=9.0 Hz, 2H), 7.32 (d, J=9.0 Hz, 2H); $^{13}$C NMR (75 MHz, CDCl$_3$) δ 12.34, 17.82, 17.91, 22.18, 23.37, 25.34, 35.89, 55.50, 57.33, 76.34, 114.52, 118.73, 131.00, 156.29, 165.58; IR (KBr) 2946, 1742, 1513, 1458, 1249 cm$^{-1}$. Anal. Calcd for C$_{23}$H$_{39}$NO$_3$Si: C, 68.10; H, 9.70; N, 3.45. Found: C, 68.26; H, 9.85; N, 3.35.

(3R,4S)-4-(Cyclohexylmethyl)-1-(4-methoxyphenyl)-3-triisopropylsilyloxy-2-azetidinone (2b): 83%; low melting point solid; $[\alpha]D^{20}$ +43.7° (c 0.92, CHCl$_3$); $^1$H NMR (300 MHz, CDCl$_3$) δ 0.85–1.95 (m, 34H), 3.78 (s, 3H), 4.19–4.25 (m, 1H), 5.05 (d, J=5.1 Hz, 1H), 6.86 (d, J=9.0 Hz, 2H), 7.32 (d, J=9.0 Hz, 2H); $^{13}$C NMR (75 MHz, CDC$_{13}$) δ 12.15, 17.76, 17.83, 26.12, 26.22, 26.47, 32.84, 34.22, 34.51, 55.36, 56.41, 76.13, 114.30, 118.45, 130.81, 155.99, 165.55; IR (neat) 2925–2865, 1749, 1513, 1464, 1448, 1389, 1246, 1174, 1145, 1128, 939, 882, 828, 684 cm$^{-1}$. Anal. Calcd for C$_{26}$H$_{43}$NO$_3$Si: C, 70.06; H, 9.72; N, 3.14. Found: C, 69.91; H, 9.71; N, 3.02.

EXAMPLES 5–6

To a solution of 0.24 mmol of 1-(4-methoxyphenyl)-β-lactam in CH$_3$CN (20 mL) was added 0.65 mmol of CAN in 10 mL CH$_3$CN and 20 mL of water in 20 min at −15° C. After stirring for 1 hr, it was diluted with water (20 mL), and the mixture was then extracted with ethyl acetate (15 mL×2). The combined organic layer was washed with NaHSO$_3$ water (7 mL), 5% (10 mL×2), 5% Na$_2$CO$_3$ (10 mL) and brine (5 mL) in sequence. Drying, removal of the solvent in vacuo followed by decolorization with activated charcoal afforded the crude product. It was further purified by silica gel column chromatography (hexanes/ethyl acetate, 3/1) to furnish N-deprotected β-lactam.

(3R, 4S)-4-(2-Methylpropyl)-3-triisopropylsilyloxy-2-azetidinone (1c): 83%; yellow oil; $[\alpha]D^{20}$ +35.450 (c 1.33, CHCl$_3$); $^1$H NMR (300 MHz, CDCl$_3$) δ 0.93 (d, J=6.6 Hz, 3H), 0.96 (d, J=6.6 Hz, 3H), 1.05–1.25 (m, 22H), 1.52 (m, 1H), 1.67 (m, 1H), 3.78 (m, 1H), 4.96 (dd, J=4.8, 2.4 Hz, 1H), 6.02 (bs, 1H); $^{13}$C NMR (75 MHz, CDCl$_3$) δ 12.12, 17.72, 17.80, 22.29, 23.08, 25.35, 39.08, 54.45, 78.04, 170.00; IR (neat) 3238, 1759, 1465, 1184 cm$^{31}$ $^1$. Anal. Calcd for C$_{16}$H$_{33}$NO$_2$Si: C, 64.16; H, 11.1; N, 4.68. Found: C, 64.17; H, 10.96; N, 4.47.

(3R,4S)-4-(Cyclohexylmethyl)-3-triisopropylsilyloxy-2-azetidinone (1d): 85%; yellow oil; [α]$D^{20}$ +12.44° (c 1.46, CHCl$_3$); $^1$H NMR (300 MHz, CDCl$_3$) δ 0,97–1.25 (m, 32H), 1.40–1.70 (m, 2H), 3.80 (dt, J=8.4, 4.8 Hz, 1H), 4.95 (dd, J=4.8, 2.4 Hz, 1H), 6.05 (bs, 1H); $^{13}$C NMR (75 MHz, CDCl$_3$) δ 12.06, 17.77, 17.82, 26.16, 26.25, 26.46, 33.15, 33.82, 34.85, 37.72, 53.89, 77.98, 169.98; IR (neat) 3238, 1759, 1465, 1184 cm$^{-1}$. Anal. Calcd for C$_{19}$H$_{37}$NO$_2$Si: C, 67.20; H, 10.98; N, 4.12. Found: C, 67.40; H, 10.79; N, 3.98.

EXAMPLES 7–11

To a solution of 2.6 mmol of 3-triisopropylsilyloxy-4-substituted-2-azetidinone in 20 mL of THF, was added at room temperature 3.1 mmol (IM in THF) of NBU$_4$F. After 5 h, the solvent was evaporated and the crude oil was directly purified by chromatography on silica gel using 5:1 EtAcO/hexanes to afford of 3-hydroxy-4-substituted-2-azetidinone:

(3R, 4S)-3-Hydroxy-4-phenyl-2-azetidinone (3a): 100%; white solid; mp 189–190° C.; [α]$D^{20}$ +181.6° (c 0.5, CH$_3$OH); $^1$H NMR (300 MHz, CD$_3$OD) δ 4.84 (d, J=4.7 Hz, 1H), 5.04 (d, J=4.7 Hz, 1H), 7.25–7.35 (m, 5H); IR (KBr) 3373, 3252, 1732, 1494 cm$^{-1}$. Anal. Calcd for C$_9$H$_9$NO$_2$: C$_{66.25}$%, H 5.56%, N 8.58%. Found: C$_{66.42}$%, H 5.74%, N 8.62%.

(3R,4S)-3-Hydroxy-4-(2-phenylethenyl)-2-azetidinone (3b): 82%; white solid; mp 143–144° C.; [α]$D^{20}$ +21.90° (c 1.05, MeOH); $^1$H NMR (300 MHz, CD$_3$OD) δ 4.35 (ddd, J=0.8, 4.7, 7.7 Hz, 1H), 4.93 (d, J=4.7 Hz, 1H), 6.28 (dd, J=7.7, 16.0 Hz, 1H), 7.18–7.43 (m, 5H); $^{13}$C NMR (75 MHz, CD$_3$OD) δ 58.95, 79.63, 126.83, 127.58, 128.88, 129.61, 135.28, 137.96, 172.79; IR (KBr) 3320, 3276, 1754, 1464 cm$^{-1}$. Anal. Calcd for C$_{11}$H$_{11}$NO$_2$: C, 69.83; H, 5.86; N, 7.40. Found: C, 69.72; H, 5.92; N, 7.24.

(3R,4S)-3-Hydroxy-4-(2-methylpropyl)-2-azetidinone (3c): 94%; white solid; mp 141–142° C.; [α]$D^{20}$ +26.60 (c 0.70, MeOH); $^1$H NMR (300 MHz, MeOH-d4) d 0.94 (d, J=6.8 Hz, 3H), 0.97 (d, J=6.8 Hz, 3H), 1.45 (m, 2H), 1.71 (sept, J=6.6 Hz, 1H), 3.75 (m, 1H), 4.79 (d, J=4.7 Hz, 1H); $^{13}$C NMR (75 MHz, MeOH-d4) δ 22.62, 23.48, 26.53, 39.90, 55.47, 77.76, 173.18; IR (KBr) 3274, 3178, 1762, 1685, 1155 cm$^{-1}$. Anal. Calcd for C$_7$H$_{13}$NO$_2$: C, 58.72; H, 9.15; N, 9.78. Found: C, 58.55; H, 9.41; N, 9.69.

(3R,4S)-4-(Cyclohexylmethyl)-3-hydroxy-2-azetidinone (3d): 92%; white solid; mp 147–148° C.; [α]$D^{20}$ +8.730 (c, 0.573, CH$_3$OH); $^1$H NMR (300 MHz, MeOH-d4) δ 0.88–1.82 (m, 13H), 3.78 (m, 1H), 4.79 (d, J=4.7 Hz, 1H); $^1$H NMR (300 MHz, DMSO-d6) δ 0.86–1.72 (m, 13H), 3.58 (m, 1H), 4.63 (m, 1H), 5.82 (d, J=7.6 Hz, 1H), 8.13 (d, J=5.6, 1H); $^{13}$C NMR (75 MHz, MeOH-d4) δ 27.29, 27.41, 27.48, 34.07, 35.06, 36.11, 38.52, 55.02, 77.65, 173.22; IR (KBr) 3301, 3219, 2915, 2847, 1754, 1694, 1168 cm$^{-1}$. Anal. Calcd for C$_{10}$H$_{17}$NO$_2$: C, 65.54, H, 9.35, N, 7.64. Found: C, 65.72, H, 9.46, N, 7.42.

(3R, 4S)-4-cyclohexyl-3-hydroxy-2-azetidinone (3e): A suspension of 500 mg (3.06 mmol) of 4-phenyl-3-hydroxy-2-azetidinone 1a and 15 mg of Rh-C in 10 mL of methanol was heated at 90° C. under 800 psi in an autoclave. After 5 days, the hydrogen pressure was released and the catalyst filtrated on celite. Evaporation of the solvent afforded a solid which was recrystallized in ethyl acetate to give 440 mg (85%) of 3e as a white solid: White solid; mp 140–140.5° C.; [α]$D^{20}$ +65.1° (c 0.66, CH$_3$OH); $^1$H NMR (250 MHz, MeOH-d$_4$) δ 0.75–1.10 (m, 2H), 1.12–1.35 (m, 3H), 1.40–2.00 (m, 6H), 3.28 (dd, J=9.7, 4.6 Hz, 1H), 4.81 (d, J=4.6 Hz, 1H); $^1$H NMR (250 MHz, DMSO-d$_6$) δ 0.75–1.00 (m, 2H), 1.10–1.35 (m, 3H), 1.37–1.55 (m, 1H), 1.58–1.85 (m, 5H), 3.10 (dd, J=9.6, 4.7 Hz, 1H), 4.67 (in, 1H), 5.87 (d, J=7.8 Hz, 1H), 8.21 (bs, 1H); $^{13}$C NMR (63 MHz, DMSO-d$_6$) δ 25.08, 25.36, 26.07, 28.83, 29.17, 37.51, 59.04, 76.41, 170.21; IR (KBr) 3312, 3219, 2928, 1726 cm$^{-1}$. Anal. Calcd for C$_9$H$_{15}$NO$_2$: C, 63.88, H, 8.93, N, 8.28. Found: C, 63.70, H, 9.00, N, 8.06.

EXAMPLES 12–16

To a solution of 1.9 mmol of 3-hydroxy-4-substituted-2-azetidinone in 20 mL of THF, was added at 0° C. 3.9 mmol of ethylvinylether. After 2 h, at 0° C., the reaction mixture was diluted with ether and washed with saturated. NaHCO$_3$. The organic layer was dried over Na$_2$CO$_3$, filtered and concentrated to yield of 3-(1-ethoxyethoxy)-4-substituted-2-azetidinone:

(3R,4S)-3-(1-Ethoxyethoxy)-4-phenyl-2-azetidinone (4a): 100%; white solid; mp 78–80° C.; $^1$H NMR (CDCl$_3$) δ [0.98 (d, J=5.4 Hz), 1.05 (d, J=5.4 Hz), 3H], [1.11 (t, J=7.1 Hz), 1.12 (t, J=7.1 Hz), 3H], [3.16–3.26 (m), 3.31–3.42 (m), 3.59–3.69 (m), 2H], [4.47 (q, J=5.4 Hz), 4.68 (q, J=5.4 Hz), 1H], [4.82 (d, J=4.7 Hz), 4.85 (d, J=4.7 Hz), 1H], 5.17–5.21 (m, 1H), 6.42 (bd, 1H), 7.35 (m, 5H); IR (KBr) 3214, 2983, 2933, 1753, 1718, 1456 cm$^{-1}$. Anal. Calcd for C$_{13}$H$_{17}$NO$_3$: C, 66.36; H, 7.28; N, 5.95. Found: C, 66.46; H, 7.11; N, 5.88.

(3R,4S)-3-(1-Ethoxyethoxy)-4-(2-phenylethenyl)-2-azetidinone(4b): 98%; white solid; mp 98–99° C.; $^1$H NMR (300 MHz, CDCl$_3$) δ [1.17 (t, J=7.1 Hz), 1.18 (t, J=7.1 Hz), 3H], [1.26 (d, J=5.4 Hz), 1.35 (d, J=5.4 Hz), 3H], [3.44–3.52 (m), 3.60–3.68 (m), 3.75–3.82 (m), 2H], 4.41 (dd, J=4.9, 8.5 Hz, 1H), [4.81 (q, J=5.4 Hz), 4.90 (q, J=5.4 Hz), 1H], [5.11 (d, J=4.9 Hz), 5.12 (d, J=4.9 Hz), 1H], 6.01 (bs, 1H), [6.27 (dd, J=8.5, 15.9 Hz), 6.28 (dd, J=8.5, 15.9 Hz), 1H], [6.61 (d, J=15.9 Hz), 6.63 (d, J=15.9 Hz), 1H], 7.27–7.42 (m, 5H); $^{13}$C NMR (75 MHz, CDCl$_3$) δ 15.04, 20.37, 20.42, 57.22, 57.81, 61.23, 62.22, 78.77, 79.29, 99.50, 99.82, 125.56, 125.79, 126.59, 128.12, 128.65, 134.47, 134.58, 136.15, 168.59, 168.77; IR (KBr) 3310, 3030, 2963, 1770 cm$^{-1}$. Anal. Calcd for C$_{15}$H$_{19}$NO$_3$: C, 68.94; H, 7.33; N, 5.36. Found: C, 69.13; H, 7.44; N, 5.16.

(3R,4S)-3-(1-Ethoxyethoxy)-4-(2-methylpropyl)-2-azetidinone (4c): 100%; colorless oil: [α]$D^{20}$ +20.930 (c 1.72, CHCl$_3$); $^1$H NMR (300 MHz, CDCl$_3$) δ 0.86 (d, J=6.5 Hz, 3H), 0.92 (d, J=6.5 Hz, 3H), 1.17 (t, J=7.0 Hz, 3H), [1.29 (d, J=5.3 Hz), 1.34 (d, J=5.3 Hz), 3H], 1.46 (m, 2H), 1.62 (m, 1H), [3.49 (m), 3.69 (m), 2H)], 3.80 (m, 1H), [4.79 (q, J=5.4 Hz), 4.90 (q, J=5,4 Hz), 1H], 4.87 (m, 1H), 6.78 (bs, 1H); $^{13}$C NMR (75 MHz, CDCl$_3$) δ 15.08, 20.42, (21.98, 22.06), (23.15, 23.22), 25.35, (39.01, 39.10), (53.35, 53.69), (61.24, 62.24), (77.79, 77.92), (99.75, 100.05), (169.56, 169.65); IR (neat) 3269, 2956, 2871, 1758, 1468, 1382, 1340, 1152, 1115, 1083, 1052, 936, 893 cm$^{-1}$.

(3R,4S)-4-(Cyclohexylmethyl)-3-(1-ethoxyethoxy)-2-azetidinone (4d): 100%; colorless oil; [α]$D^{20}$ +10.92° (c 1.42, CHCl$_3$); $^1$H NMR (300 MHz, CDCl$_3$) δ 0.84–1.71 (m, 13H), 1.16 (t, J=7.0 Hz, 3H), (1.28 (d, J=5.3 Hz), 1.33 (d, J=5.3 Hz), 3H], 3.48 (m, 1H), [3.72 (m), 3.8 (m), 2H], [4.78 (q, J=5.4 Hz), 4.85 (q, J=5.4 Hz), 1H], 4.82 (m, 1H), 6.76 (bs, 1H); $^{13}$C NMR (75 MHz, CDCl$_3$) δ 14.37, 19.72, 25.30, 25.44, 25.63, (32.02, 32.13), (33.09, 33.17), (34.03, 34.07), (36.98, 37.07), (52.15, 52.49), (60.49, 61.52), (75.97, 76.39), (99.00, 99.35), (168.98, 169.05); IR (neat) 3278, 2924, 2852, 1758, 1448,1382, 1150, 1114, 1086, 938, 886 cm$^{-1}$. Anal. Calcd for C$_{14}$H$_{25}$NO$_3$: C, 65.85; H, 9.87; N, 5.49. Found: C, 66.03; H, 9.71; N, 5.30.

(3R,4S)-4-Cyclohexyl-3-(1-ethoxyethoxy)-2-azetidinone (4e): 100%; white solid; mp 87–89° C.; [α]$D^{20}$ +83° (c 0.76, CH₃OH); ¹H NMR (250 MHz, CDCl₃) δ 0.84 (m, 2H), 1.07–1.34 (m, 9H), 1.66 (m, 6H), 3.32 (m, 1H), [3.42 (q, J=7.7 Hz), 3.54 (q, J=7.7 Hz), 3.65 (q, J=7.7 Hz), 3.74 (q, J=7.7 Hz), 2H], 4.81 (m, 1H), [4.80 (m), 4.90 (q, J=5.2 Hz), 1H], 6.92 (bs, 1H); IR (CHCl₃) 3412, 2989, 2931, 1760, 1443, 1155, 1114 cm⁻¹. Anal. Calcd for $C_{13}H_{27}NO_3$: C, 64.70; H, 9.61; N, 5.80. Found: C, 64.82; H, 9.66; N, 5.64.

EXAMPLES 17–27

To a solution of 2.2 mmol of 3-(1-ethoxyethoxy)-4-substituted-2-azetidinone, 5 mg of DMAP, 4.5 mmol of triethylamine in 20 mL of dichloromethane, was added dropwise at 0° C. 3.3 mmol of alkylchloroformate dissolved in 5 mL of dichloromethane. The reaction mixture was stirred overnight at room temperature. The organic layer was washed several times with brine, dried over Na₂CO₃ and concentrated. The crude solid was purified by chromatography on silica gel to yield N-protected β-lactam:

(3R, 4S)-1-Methoxycarbonyl-3-(1-ethoxyethoxy)-4-phenyl-2-azetidinone (5a): 62%; pale yellow oil; [α]D²⁰ +98.20 (c 1.1, CHCl₃); ¹H NMR (250 MHz, CDCl₃) δ [0.97 (d, J=5.4 Hz), 1.08 (d, J=5.4 Hz), 3H], 1.10 (bt, J=7.3 Hz, 3H), [3.21 (dq, J=9.5, 7.1 Hz), 3.32 (q, J=7.1 Hz), 3.64 (dq, J=9.5, 7.1 Hz), 2H], [3.76 (s), 3.77 (s), 3H], [4.48 (q, J=5.4 Hz), 4.69 (q, J=5.4 Hz), 1H], [5.11 (d, J=5.9 Hz), 5.14 (d, J=5.9 Hz), 1H], 5.23 (d, J=5.9 Hz, 1H), 7.34 (m, 5H); ¹³C NMR (63 MHz, CDCl₃) δ (14.96, 15.07), (19.84, 20.69), 53.59, (60.74, 62.36), (61.14, 61.92), (76.21, 77.21), (99.16, 99.56), (127.73, 128.03, 128.31, 128.36, 128.62, 128.85), (133.41, 133.58), (149.51, 149.57), (165.21, 165.67); IR (neat) 3033, 2979, 2957, 1821, 1738, 1654, 1440, 1336, 1101 cm⁻¹. Anal. Calcd for $C_{15}H_{19}NO_5$: C, 61.42; H, 6.53; N, 4.78. Found: C, 61.55; H, 6.51; N, 4.90.

(3R, 4S)-1-Ethoxycarbonyl-3-(1-ethoxyethoxy)-4-phenyl-2-azetidinone (5b): 82%; colorless oil; [α]D²⁰ +100.9° (c 1.08, CHCl₃); ¹H NMR (250 MHz, CDCl₃) δ [0.95 (d, J=5.4 Hz), 1.06 (d, J=5.4 Hz), 3H], 1.08 (bt, J=7.3 Hz, 3H), [1.19 (t, J=7.1 Hz), 1.20 (t, J=7.1 Hz), 3H], [3.20 (dq, J=9.4, 7.1 Hz), 3.31 (q, J=7.1 Hz), 3.32 (q, J=7.1 Hz), 3.63 (dq, J=9.4, 7.1 Hz), 2H], [4.18 (q, J=7.1 Hz), 4.19(q, J=7.1 Hz), 2H], [4.47 (q, J=5.4 Hz), 4.67 (q, J=5.4 Hz), 1H], [5.09 (d, J=5.8 Hz), 5.13 (d, J=5.8 Hz), 1H], 5.21 (d, J=5.8 Hz, 1H), 7.30 (m, 5H); ¹³C NMR (63 MHz, CDCl₃) δ 14.14, (14.95, 15.07), (19.86, 20.05), (60.76, 62.35), 62.36, (61.14, 61.90), (76.18, 77.20), (99.17, 99.53), (127.73, 128.02, 128.25, 128.30, 128.50, 128.63), (133.59, 133.77), (148.99, 149.05), (165.33, 165.79); IR (neat) 2978, 2934, 1814, 1731, 1646, 1540, 1456, 1323, 1175, 1096 cm⁻¹. Anal. Calcd for $C_{16}H_{21}NO_5$: C, 62.53; H, 6.89; N, 4.56. Found: C, 62.45; H, 6.63; N, 4.83.

(3R, 4S)-1-n-Butoxycarbonyl-3-(1-ethoxyethoxy)-4-phenyl-2-azetidinone (5c): 83%; colorless oil; [α]D²⁰ +70.40 (c 1.25, CHCl₃); ¹H NMR (250 MHz, CDCl₃) δ 0.79 (t, J=7.3 Hz, 3H), [0.94 (d, J=5.1 Hz), 1.07 (d, J=5.1 Hz), 3H], 1.07 (t, J=7.4 Hz, 3H), 1.20 (m, 2H), 1.51 (quint, J=6.7 Hz, 2H), [3.21 (m), 3.30 (q, J=7.1 Hz), 3.61 (m), 2H], 4.09 (m, 2H), [4.46 (q, J=5.2 Hz), 4.66 (q, J=5.2 Hz), 1H], [5.07 (d, J=5.8 Hz), 5.11 (d, J=5.8 Hz), 1H], 5.19 (d, J=5.8 Hz, 1H), 7.28 (m, 5H); ¹³C NMR (63 MHz, CDCl₃) δ 13.50, (14.95, 15.29), 18.71, (19.84, 20.05), 30.42, (60.77, 62.33), (61.25, 62.02), 66.51, (76.24, 77.26), (99.17, 99.52), (127.76, 128.03, 128.22, 128.27, 128.50, 128.60), (133.61, 133.80), (148.96, 149.02), (165.40, 165.85); IR (neat) 2961, 2933, 1817, 1732, 1653, 1456, 1394, 1250, 1099 cm⁻¹. Anal. Calcd for $C_{18}H_{25}NO_5$: C, 64.46; H, 7.51; N, 4.18. Found: C, 64.44; H, 7.57; N, 4.24.

(3R, 4S)-1-tert-Butoxycarbonyl-3-(1-ethoxyethoxy)-4-phenyl-2-azetidinone (5d): 83%; white solid; rap 90–91° C.; [α]D²⁰ +70.40 (c 1.25, CHCl₃); ¹H NMR (250 MHz, CDCl₃) δ[0.96 (d, J=5.4 Hz), 1.08 (d, J=5.4 Hz), 3H], [1.09 (t, J=7.0 Hz), 1.10 (t, J=7.0 Hz), 3H], [1.36 (s), 1.37 (s), 9H], [3.23 (dq, J=9.5, 7.1 Hz), 3.32 (q, J=7.1 Hz), 3.65 (dq, J=9.5, 7.1 Hz), 2H], [4.48 (q, J=5.4 Hz), 4.69 (q, J=5.4 Hz), 1H], [5.03 (d, J=5.8 Hz), 5.07 (d, J=5.8 Hz), 1H], 5.18 (d, J=5.8 Hz, 1H), 7.31 (m, 5H); ¹³C NMR (63 MHz, CDCl₃) δ (14.98, 15.08), (19.89, 20.10), 27.84, (60.74, 62.32), (61.28, 62.08), (75.91, 76.54), 83.48 (99.10, 99.41), (127.76, 128.07, 128.20, 128.42, 128.85), (133.98, 134.16), 147.56, (165.61, 166.04); IR (CHCl₃) 3025, 2982, 2932, 1809, 1725, 1601, 1497, 1331, 1256, 1152 cm⁻¹. Anal. Calcd for $C_{18}H_{25}NO_5$: C, 64.46; H, 7.51; N, 4.18. Found: C, 64.50; H, 7.41; N, 4.17.

(3R, 4S)-3-(1-Ethoxyethoxy)-1-phenoxycarbonyl-4-phenyl-2-azetidinone (5e): 79%; white solid; mp 50–52° C.; [α]D²⁰ +64.9° (c 0.94, CHCl₃); ¹H NMR (250 MHz, CDCl₃) δ [1.00 (d, J=5.3 Hz), 1.11 (m), 3H], [1.14 (m), 3H], [3.27 (m), 3.35 (q, J=7.1 Hz), 3.70 (m), 2H], [4.54 (q, J=5.3 Hz), 4.74 (q, J=5.3 Hz), 1H], [5.25 (d, J=5.8 Hz), 5.29 (d, J=5.8 Hz), 1H], 5.34 (d, J=5.8 Hz, 1H), 7.03–7.39 (m, 10H); IR (CHCl₃) 3028, 2981, 2934, 1815, 1744, 1591, 1486, 1327, 1192 cm⁻¹. Anal. Calcd for $C_{20}H_{21}NO_5$: C, 67.59; H, 5.96; N, 3.94. Found: C, 67.33; H, 6.06; N, 3.75.

(3R, 4S)-3-(1-Ethoxyethoxy)-4-phenyl-1-phenylmethoxycarbonyl-2-azetidinone (5f): 44%; white solid; mp 58–60° C.; [α]D²⁰ +91.40 (c 1.16, CHCl₃); ¹H NMR (250 MHz, CDCl₃) δ [0.97 (d, J=5.3 Hz), 1.09 (d, J=5.3 Hz), 3H], [1.10 (t, J=7.0 Hz), 1.11 (t, J=7.0 Hz), 3H], [3.23 (dq, J=9.5, 7.1 Hz), 3.33 (q, J=7.1 Hz), 3.66 (dq, J=9.5, 7.1 Hz), 2H], [4.50 (q, J=5.4 Hz), 4.70 (q, J=5.4 Hz), 1H], [5.13 (d, J=5.6 Hz), 5.15 (d, J=5.6 Hz), 1H], [5.19 (s), 5.20 (s), 2H], 5.23 (d, J=5.6 Hz, 1H), 7.21 (m, 2H), 7.26–7.37 (m, 8H); ¹³C NMR (63 MHz, CDCl₃) δ (14.99, 15.10), (19.90, 20.10), (60.83, 62.41), (61.64, 62.14), 68.01, (76.31, 77.28), (99.19, 99.53), (127.37, 127.86, 128.07, 128.16, 128.36, 128.52, 128.63, 128.85), (133.49, 133.68), 134.89, (148.72, 148.78), (165.37, 165.81); IR (CHCl₃) 3028, 2981, 2934, 1815, 1733, 1604, 1450, 1380, 1004 cm⁻¹. Anal. Calcd for $C_{21}H_{23}NO_5$: C, 68.28; H, 6.28; N, 3.79. Found: C, 68.07; H, 6.43; N, 3.72.

(3R,4S)-1-tert-Butoxycarbonyl-4-cyclohexyl-3-(1-ethoxyethoxy)-2-azetidinone (5g): 91%; colorless oil; [α]D²⁰ +62.50 (c 1.12, CHCl₃); H NMR (250 MHz, CDCl₃) δ 1.10–1.28 (m, 6H), 1.15 (t, J=7.0 Hz, 3H), [1.27 (d, J=5.4 Hz), 1.31 (d, J=5.4 Hz), 3H], [1.45 (s), 1.46 (s), 9H], 1.63–1.70 (m, 5H), [3.43 (dq, J=9.2, 7.0 Hz), 3.62 (m), 3.75 (d, J=7.0 Hz), 3.78 (d, J=7.0 Hz), 2H], 3.85 (t, J=6.1 Hz, 1H), [4.78 (q, J=5.4 Hz), 4.88 (m), 1H], [4.85 (d, J=6.1 Hz), 4.86 (d, J=6.1 Hz), 1H]; ¹³C NMR (63 MHz, CDCl₃) δ 15.07, (20.25, 20.37), (26.05, 26.14), 26.26, (27.33, 27.95), (29.05, 29.20), (30.04, 30.23), (37.54, 37.64), (61.19, 62.53), (62.06, 62.32), (75.42, 75.85), 83.06, 100.11, 148.72, (166.70, 166.76); IR (neat) 2980, 2931, 2854, 1807, 1725, 1450, 1370, 1329, 1212, 1118 cm.⁻¹. Anal. Calcd for $C_{18}H_{31}NO_5$: C, 63.32; H, 9.15; N, 4.10. Found: C, 63.15; H. 8.97; N, 3.96.

(3R, 4S)-1-tert-Butoxycarbonyl-3-(1-ethoxyethoxy)-4-(2-phenylethenyl)-2-azetidinone (5h): 86%; white solid; mp 69–73° C.; ¹H NMR (300 MHz, CDCl₃) δ [1.16 (t, J=7.1 Hz), 1.18 (t, J=7.1 Hz), 3H], [1.25 (d, J=5.4 Hz), 1.36 (d, J=5.4 Hz), 3H], 1.48 (s, 9H), [3.47 (m), 3.62 (m), 3.80 (m), 2H], 4.68 (dd, J=5.8, 8.8 Hz, 1H), [4.82 (q, J=5.4 Hz), 4.91 (q, 5.4 Hz), 1H], [5.09 (d, J=5.8 Hz), 5.11 (d, J=5.8 Hz), 1H], [6.23 (dd, J=8.8, 15.8 Hz), 6.25 (dd, J=8.8, 15.8 Hz), 1H], [6.72 (d, J=15.8 Hz), 6.73 (d, J=15.8 Hz), 1H], 7.27–7.44 (m, 5H); ¹³C NMR (75 MHz, CDCl₃) δ 14.98, 20.31, 27.98, 60.24, 60.85, 61.46, 62.36, 63.58, 83.38, 99.63, 99.87, 122.45, 122.63, 126.69, 128.20, 128.61, 136.15, 136.34, 136.38, 147.74, 147.79, 165.33, 165.53; IR (KBr) 3027, 3020, 2984, 2933, 1809, 1723 cm$^{-1}$. Anal. Calcd for $C_{20}H_{27}NO_5$: C, 66.46; H, 7.53; N, 3.88. Found: C, 66.60; H, 7.50; N, 3.87.

(3R, 4S)-1-tert-Butoxycarbonyl-3-(1-ethoxyethoxy)-4-(2-methylpropyl)-2-azetidinone (5i): 80%; yellow oil; $[\alpha]D^{20}$ +77.45° (c 0.216, CHCl$_3$); $^1$H NMR (300 MHz, CDCl$_3$) δ 0.89 (d, J=5.7 Hz, 6H), 1.41 (t, J=7.1 Hz, 3H), [1.25 (d, J=5.3 Hz ), 1.31 (d, J=5.3 Hz), 3H), 1.45 (s, 9H), 1.51–1.67 (m, 3H), [3.48 (dq, J=9.3, 7.1 Hz), 3.55–3.71 (m, 1H), 3.80 (dq, J=9.3, 7.1 Hz), 2H], 4.08 (q, J=6.1 Hz, 1H), [4.70 (q, J=5.3 Hz ), 4.90 (q, J=5.3 Hz), 1H], 4.85 (d, J=6.1 Hz, 1H); $^{13}$C NMR (75 MHz, CDCl$_3$) δ 14.95, (20.11, 20.28), (22.42, 22.59), 22.70, (24.89, 25.07), 27.83, (37.03, 37.31), (56.14, 56.38), (61.07, 62.27), (75.65, 75.92), 82.98, 99.91, 148.1, (166.1, 165.9); IR (neat) 2931, 2960, 2872, (1790, 1807), (1708, 1726), (1454, 1465), 1332, 1256, 1048, 1158, 996, 955, 857, 834, 770 cm$^{-1}$. Anal. Calcd for $C_{16}H_{26}NO_5$: C, 60.93; H, 9.27; N, 4.44. Found: C, 61.19; H, 9.41; N, 4.37.

(3R, 4S)-1-tert-Butoxycarbonyl-4-cyclohexylmethyl-3-(1-ethoxyethoxy)-2-azetidinone (5j): 93%; yellow oil; $[\alpha]D^{20}$ +75.640 (c 0.78, CHCl$_3$); $^3$H NMR (300 MHz, CDCl$_3$) δ 0.81–1.74 (m, 13H), 1.19 (t, J=7.1 Hz, 3H), 1.48 (s, 9H), [1.30 (d, J=5.3 Hz), 1.35 (d, J=5.3 Hz), 3H], [3.45 (dq, J=9.3, 7.1 Hz), 3.62–3.71 (m), 3.78 (dq, J=9.3, 7.1 Hz), 2H], 4.01 (m, 1H), [4.81 (q, J=5.3 Hz), 4.91 (q, J=5.3 Hz), 1H], [4.86 (d, J=6.1 Hz), 4.87 (d, J=6.1 Hz), 1H]; $^{13}$C NMR (75 MHz, CDCl$_3$) δ 15.03, 20.19, 20.36, 26.10, 26.36, 27.91, (33.17, 33.31), (33.35, 33.49), (34.33, 34.58), (35.39, 35.68), (55.77, 55.99), (61.14, 62.21), (75.74, 75.90), 82.96, (99.86, 99.95), 147.96, 166.13; IR (neat) 2979, 2923, 2850, 1719, 1807, 1449, 1336, 1154 cm$^{-1}$. Anal. Calcd. for $C_{19}H_{33}NO_5$: C, 64.20; H, 9.36; N, 3.94. Found: C, 64.00; H, 9.17; N, 4.02.

EXAMPLES 28–32

To a solution of 0.5 mmol of 3-(1-ethoxyethoxy)-4-phenyl-2-azetidinone in 6 mL of tetrahydrofuran, was added dropwise at −78° C. 0.6mmol of n-BuLi. After 5 min, 1 mmol of an isocyanate or an isothiocyanate was added. The reaction mixture was stirred 30 min at −78° C. and quenched by addition of 2 mL sat. NH$_4$Cl solution.

The reaction mixture was diluted with 30 mL of ether and the organic layer was washed several times with brine, dried over Na$_2$CO$_3$ and concentrated. The crude solid was purified by chromatography on silica gel to yield N-protected β-lactam:

(3R, 4S)-3-(1-Ethoxyethoxy)-1-phenylcarbamoyl-4-phenyl-2-azetidinone (7a): 66%; pale yellow solid; mp 152–155° C.; $[\alpha]D^{20}$ +87.80 (c 0.9, CHCl$_3$); $^1$H NMR (250 MHz, CDCl$_3$) δ [1.07 (d, J=5.4 Hz), 1.13 (d, J=5.4 Hz), 3H], 1.16 (t, J=7.1 Hz, 3H), [3.26 (dq, J=9.5, 7.1 Hz), 3.37 (q, J=7.1 Hz), 3.39 (q, J=7.1 Hz), 3.67 (dq, J=9.5, 7.1 Hz), 2H], [4.53 (q, J=5.4 Hz), 4.72 (q, J=5.4 Hz), 1H], 5.28 (m, 2H), [6.59 (bs), 6.60 (bs), 1H], 7.10–7.55 (m, 10H), 8.68 (bs, 1H); $^{13}$C NMR (63 MHz, CDCl$_3$) δ (15.04, 15.16), (19.98, 20.11), (60.99, 62.53), 61.80, (76.05, 76.66), (99.34, 99.70), (119.63, 120.69, 124.37, 127.67, 127.95, 128.40, 128.45, 128.67, 128.85, 129.04, 129.12, 130.49), 133.48, (137.03, 137.28), (147.23, 147.29), (168.12, 168.52); IR (CHCl$_3$) 3342, 3017, 2982, 2932, 1773, 1719, 1602, 1548, 1445, 1312, 1224, 1210 cm$^{-1}$. Anal. Calcd for $C_{20}H_{22}N_2O_4$: C, 67.78; H, 6.26; N, 7.90. Found: C, 67.92; H, 5.98; N, 8.17.

(3R, 4S)-1-tert-Butylcarbamoyl-3-(1-ethoxyethoxy)-4-phenyl-2-azetidinone (7b): 74%; pale yellow viscous oil; $[\alpha]D^{20}$ +144.30 (c 0.7, CHCl$_3$); $^1$H NMR (250 MHz, CDCl$_3$) δ [0.96 (d, J=5.3 Hz), 1.05 (d, J=5.3 Hz), 3H], 1.10 (t, J=7.1 Hz, 3H), [1.33 (s), 1.34 (s), 9H], [3.21 (dq, J=9.3, 7.0 Hz), 3.30 (q, J=7.0 Hz), 3.33 (q, J=7.1 Hz), 3.62 (dq, J=9.1, 7.0 Hz), 2H], (4.46 (q, J=5.4 Hz), 4.66 (q, J=5.4 Hz), 1H], 5.10–5.19 (m, 2H), [6.59 (bs), 6.60 (bs), 1H], 7.23–7.36 (m, 5H); $^{13}$C NMR (63 MHz, CDCl$_3$) δ (14.86, 14.99), (19.75, 19.95), (28.81, 29.30), (60.62, 61.20), (60.80, 62.29), (75.57, 76.76), (98.91, 99.34), (127.07, 127.40, 127.70, 128.17, 128.29, 128.53), (133.71, 133.86), (148.54, 148.59), (167.67, 168.13); IR (CHCl$_3$) 3362, 3035, 2977, 2932, 1767, 1710, 1605, 1537, 1457, 1366, 1320, 1282, 1217, 1100 cm$^{-1}$. Anal. Calcd for $C_{18}H_{26}N_2O_4$: C, 64.65; H, 7.84; N, 8.38. Found: C, 64.46; H, 7.75; N, 8.39.

(3R, 4S)-1-Benzylcarbamoyl-3-(1-ethoxyethoxy)-4-phenyl-2-azetidinone (7c): 50%; pale yellow viscous oil; $[\alpha]D^{20}$ +66.2° (c 0.8, CHCl$_3$); $^1$H NMR (250 MHz, CDCl$_3$) δ [0.99 (d, J=5.5 Hz), 1.08 (d, J=5.5 Hz), 3H], 1.12 (m, 3H), [3.16–3.40 (m), 3.63 (m), 2H], [4.35–4.55 (m), 4.69 (q, J=5.5 Hz), 3H], 5.21 (m, 2H), [7.03 (bs), 7.05 (bs), 1H], 7.32 (m, 10H); $^{13}$C NMR (63 MHz, CDCl$_3$) δ (15.01, 15.14), (19.90, 20.11), 43.83, (60.66, 62.44), (60.75, 61.54), (75.93, 77.04), (99.16, 99.56), (127.25, 127.64, 127.69, 128.17, 127.93, 128.35, 128.55, 128.64, 128.74), (133.59, 133.76), 137.80, 150.02, (167.73, 168.19); IR (CHCl$_3$) 3379, 3090, 3033, 2980, 2930, 1773, 1707, 1604, 1536, 1455, 1319, 1270, 908 cm$^{-1}$. Anal. Calcd for $C_{21}H_{24}N_2O_4$: C, 68.46; H, 6.57; N, 7.60. Found: C, 68.30; H, 6.66; N, 7.51.

(3R, 4S)-3-(1-Ethoxyethoxy)-1-ethylcarbamoyl-4-phenyl-2-azetidinone (7d): 63%; pale yellow oil; $[\alpha]D^{20}$ +96.70 (c 0.9, CHCl$_3$); $^1$H NMR (250 MHz, CDCl$_3$) δ [0.96 (d, J=5.3 Hz), 1.04 (d, J=5.3 Hz), 3H], 1.05–1.18 (m, 3H), [3.13–3.39 (m), 3.59 (m), 4H], [4.45 (q, J=5.3 Hz), 4.65 (q, J=5.3 Hz), 1H], 5.16 (m, 2H), [6.60 (bs), 6.62 (bs), 1H], 7.27 (m, 5H); $^{13}$C NMR (63 MHz, CDCl$_3$) δ 14.98, (19.84, 29.93), 34.79, (60.56, 61.35), (60.72, 62.35), (75.91, 77.03), (99.14, 99.54), (127.28, 127.55, 127.85, 128.27, 128.40), (133.74, 133.89), (149.87, 149.93), (167.62, 168.07); IR (CHCl$_3$) 3378, 3035, 2980, 2934, 1774, 1704, 1537, 1455, 1321, 1271, 1112, 1025 cm$^{-1}$.

(3R, 4S)-3-(1-Ethoxyethoxy)-1-phenylthiocarbamoyl-4-phenyl-2-azetidinone (7e): 82%; yellow solid; mp 108–112° C.; $[\alpha]D^{20}$ +680 (c 1.14, CHCl$_3$); $^1$H NMR (250 MHz, CDCl$_3$) δ [1.02 (d, J=5.5 Hz), 1.11 (d, J=5.5 Hz), 3H], 1.16 (t, J=7.3 Hz, 3H), [3.20–3.44 (m), 3.66 (dq, J=9.4, 7.3 Hz), 2H], [4.52 (q, J=5.5 Hz), 4.72 (q, J=5.5 Hz), 1H], [5.30 (d, J=5.5 Hz), 5.32 (d, J=5.5 Hz), 1H], [5.49 (d, J=5.5 Hz), 5.52 (d, J=5.5 Hz), 1H], 7.36 (m, 8H), 7.67 (d, J=7.8 Hz, 2H), 10.37 (bs, 1H); $^{13}$C NMR (63 MHz, CDCl$_3$) δ (15.04, 15.17), (19.95, 20.13), (60.96, 62.57), (63.92, 64.75), (74.75, 75.84), (99.34, 99.68), (123.43, 126.58, 127.91, 128.28, 128.49, 128.86, 128.91), (133.10, 133.25), (137.36), (166.55, 166.52), (174.812); IR (CHCl$_3$) 3288, 3024, 2983, 1760, 1497, 1385, 1222 cm$^{-1}$.

EXAMPLES 33–34

(3R,4S)-1-Morpholinecarbonyl-3-(1-ethoxyethoxy)-4-phenyl-2-azetidinone (7f): To a solution of 30 mg (0.13 mmol) of 3-(1-ethoxyethoxy)-4-phenyl-2-azetidinone 6 in 2 mL of CH$_2$Cl$_2$, 2 mg of DMAP and 0.05 mL of triethylamine was added at room temperature. After 5 min, 22.9 mg (0.15 mmol) of morpholinecarbonyl chloride was added. The reaction mixture was stirred for 2 h at room temperature. The reaction mixture was diluted with 20 mL of CH$_2$Cl$_2$ and the organic layer was washed two times with brine, dried over Na$_2$CO$_3$ and concentrated. The crude solid product was purified by chromatography on silica gel to yield pure 7f: 87%; pale yellow oil; $^1$H NMR (250 MHz, CDCl$_3$) δ [0.90

(d, J=5.3 Hz), 1.01 (d, J=5.3 Hz) (3H)], [1.04 (t, J=7.1 Hz), 1.18 (t, J=7.1 Hz)] (3H), 3.20 (m, 4H), [3.28 (m), 3.53 (m), 3.67 (m) (2H)], 3.60 (m, 4H), [4.41 (g, J=5.3 Hz), 4.63 (q, J=5.3 Hz) (1H)], [5.07 (d, J=5.8 Hz), 5.08 (d, J=5.8 Hz) (1H)], [5.29 (d, J=5.8 Hz), 5.32 (d, J=5.8 Hz) (1H)], 7.23–7.27 (m, 5H).

EXAMPLES 35–53

To a solution of 0.37 mmol of O-EE-β-lactam in 4 mL THF was added 4 mL of 0.5 N HCl. The completion of reaction was monitored by TLC. After 1–3 hr, the reaction mixture was concentrated in vacuo to remove THF. The residue was dissolved in 30 mL ether and washed with 10 mL saturated $NaHCO_3$ solution. The ether layer was washed with brine, dried over anhydrous sodium sulfate, and concentrated in vacuo to give 3-hydroxy-β-lactam:

(3R,4S)-3-Hydroxy-1-methoxycarbonyl-4-phenyl-2-azetidinone (6a): 66%; white solid; mp ; 91–92° C. $[\alpha]D^{20}$ +108° (c 0.63, $CHCl_3$); $^1H$ NMR (250 MHz, $CDCl_3$) δ 3.80 (s, 3H), 5.13 (d, J=6.0 Hz, 1H), 5.22 (d, J=6.0 Hz, 1H), 7.25–7.42 (m, 5H); $^{13}C$ NMR (63 MHz, $CDCl_3$) δ 53.77, 61.44, 77.33, 127.16, 128.94, 132.65, 149.20, 166.04; IR ($CHCl_3$) 3432, 3024, 2996, 1806, 1730, 1440, 1333, 1188 cm$^{-1}$. MS(FAB) m/z (%) 222 (M+1, 38), 194(29), 164(100).

(3R,4S)-1-Ethoxycarbonyl-3-hydroxy-4-phenyl-2-azetidinone (6b): 59%; white solid; mp 112–113° C.; $[\alpha]D^{20}$ +181° (c 0.97, $CHCl_3$); $^1H$ NMR (250 MHz, $CDCl_3$) δ 1.27 (t, J=7.1 Hz, 3H), 4.25 (q, J=7.1 Hz, 2H), 5.14 (d, J=6.0 Hz, 1H), 5.22 (d, J=6.0 Hz, 1H), 7.27–7.39 (m, 5H); $^{13}C$ NMR (63 MHz, $CDCl_3$) δ 14.08, 61.36, 63.00, 77.26, 127.08, 128.83, 132.75, 149.08, 165.79; IR ($CHCl_3$) 3605, 3017, 2985, 1815, 1732, 1684, 1396, 1373, 1268, 1020 cm$^{31}$ ; MS (FAB) m/z (%) 236 (M+1,98), 208(23), 178(100).

(3R, 4S)-1-n-Butoxycarbonyl-3-hydroxy-4-phenyl-2-azetidinone (6c): 69%; white solid; mp 88–89° C.; $[\alpha]D^{20}$ +159.10 (c 0.71, $CHCl_3$); $^1H$ NMR (250 MHz, $CDCl_3$) δ 0.78 (t, J=7.3 Hz, 3H), 1.14 (m, 2H), 1.50 (m, 2H), [4.07 (q. J=8.9 Hz), 4.10 (q, J=8.9 Hz), 2H), 5.05 (d, J=5.9 Hz, 1H); 5.11 (d, J=5.9 Hz, 1H), 7.22–7.36 (m, 5H); $^{13}C$ NMR (63 MHz, $CDCl_3$) δ 13.44, 18.71, 30.44, 61.54, 66.72, 77.31, 127.21, 128.80, 132.89, 149.15, 166.06; IR ($CHCl_3$) 3562, 3018, 2962, 1813, 1730, 1456, 1395, 1324, 1222, 1099 cm$^4$. MS (FAB) m/z (%) 264(M+1,62), 236(20), 208(40), 206(100).

(3R, 4S)-1-tert-Butoxycarbonyl-3-hydroxy-4-phenyl-2-azetidinone (6d): 88%; white solid; mp 131.5–132° C.; $[\alpha]D^{20}$ +173.5° (c 0.98, $CHCl_3$); $^1H$ NMR (250 MHz, $CDCl_3$) δ 1.40 (s, 9H), 2.70 (bs, 1H), 5.08 (d, J=5.9 Hz, 1H), 5.14 (d, J=5.9 Hz, 1H), 7.27 (d, J=6.1 Hz, 2H), 7.38 (m, 3H); $^{13}C$ NMR (63 MHz, $CDCl_3$) δ 27.87, 61.56, 77.00, 83.85, 127.20, 128.77, 128.82, 133.13, 147.72, 169.49; IR ($CHCl_3$) 3616, 3019, 2976, 1807, 1726, 1601, 1522, 1422, 1333, 1212, 1152 cm$^{-1}$. Anal. Calcd for $C_{14}H_{17}NO_4$: C, 63.87; H, 6.51; N, 5.32. Found: C, 63.71; H, 6.38; N, 5.12.

(3R, 4S)-3-Hydroxy-1-phenoxycarbonyl-4-phenyl-2-azatidinone (6e): 72%; white solid; mp 125–126° C.; $[\alpha]D^{20}$ +107° (c 1.45, $CHCl_3$); $^1H$ NMR (250 MHz, $CDCl_3$) δ 5.21 (d, J=6.1 Hz, 1H), 5.34 (d, J=6.1 Hz, 1H), 7.07–7.45 (m, 10H); $^{13}C$ NM (63 MHz, $CDCl_3$) δ 61.83, 73.24, 121.15, 125.46, 126.80, 127.22, 128.09, 128.80, 129.11, 129.30, 132.40, 138.49, 154.05; IR ($CHCl_3$) 3615, 3020, 2976, 1821, 1740, 1506, 1487, 1332, 1219 cm$^{-1}$.

(3R, 4S)-1-Benzyloxycarbonyl-3-hydroxy-4-phenyl-2-azetidinone(6f): 85%; white solid; mp 105–106° C.; $[\alpha]D^{20}$ +1770 (c 0.6, $CHCl_3$); $^1H$ NMR (250 MHz, $CDCl_3$) δ 5.12 (d, J=6.2 Hz, 1H), 5.22 (m, 3H), 7.24–7.40 (m, 10H); $^{13}C$ NMR (63 MHz, $CDCl_3$) δ 61.53, 68.30, 77.43, 127.19, 128.13, 128.58, 129.06, 132.55, 134.74, 148.90, 165.92; IR ($CHCl_3$) 3557, 3018, 2924, 1814, 1731, 1383, 1273, 1162, 1004 cm$^{-1}$. MS (FAB) n/z (%) 298(M+1,14), 273(4).

(3R, 4S)-1-tert-Butoxycarbonyl-4-cyclohexyl-3-hydroxy-2-azetidinone (6g): 96%; white solid; mp 121–122° C.; $[\alpha]D^{20}$ +78° (c 0.68, $CHCl_3$); $^1H$ NMR (250 MHz, $CDCl_3$) δ 1.17–1.75 (m, 11H), 1.48 (s, 9H), 3.83 (t, J+6.5 Hz, 1H), 4.96 (d, J=6.5 Hz, 1H); $^{13}C$ NMR (63 MHz, $CDCl_3$) δ 25.87, 25.99, 26.24, 27.96, 29.69, 29.90, 37.45, 63.30, 75.24, 83.43, 148.80, 168.60; IR ($CHCl_3$) 3354, 2931, 2848, 1801, 1724, 1324, 1154 cm$^{-1}$.

(3R,4S)-1-tert-Butoxycarbonyl-3-hydroxy-4-(2-phenylethenyl)-2-azetidinone (6h): 96%; white solid; mp 132–133° C.; $[\alpha]D^{20}$ +122.00 (c 1.1, $CHCl_3$); $^1H$ NMR (300 MHz, $CDCl_3$) δ 1.47 (s, 9H), 3.88 (bs, 1H), 4.71 (dd, J=4.8, 8.0 Hz, 1H), 5.07 (d, J=4.8 Hz, 1H), 6.26 (dd, J=8.0, 15.9 Hz, 1H), 6.72 (d, J=15.9 Hz, 1H), 7.24–7.43 (m, 5H); $^{13}C$ NMR (75 MHz, $CDCl_3$) δ 27.94, 60.78, 76.58, 83.77, 121.41, 126.75, 128.26, 128.59, 135.94, 136.62, 147.85, 166.95; IR (KBr) 3242, 3039, 2954, 1812, 1726 cm$^{-1}$. Anal Calcd for $C_{16}H_{19}NO_4$: C, 66.42; H, 6.62; N, 4.84. Found: C, 66.31; H, 6.71; N, 4.76.

(3R,4S)-1-tert-Butoxycarbonyl-3-hydroxy-4-(2-methylpropyl)-2-azetidinone (6i): 98%; pale yellow solid; mp 108° C.; $[\alpha]D^{20}$ +76.14° (c 0.88, $CHCl_3$); $^1H$ NMR (300 MHz, $CDCl_3$) δ 0.93 (d, J=6.3 Hz, 6H), 1.48 (s, 9H), 1.62–1.82 (m, 3H), 4.12 (m, 1H), 4.30 (bs, 1H), 4.93 (d, J=5.9 Hz, 1H); $^{13}C$ NMR (75 MHz, $CDCl_3$) δ 22.45, 22.78, 25.12, 27.96, 36.28, 57.59, 75.39, 83.46, 148.13, 168.00; IR (KBr) 3363, 2960, 2926, 1733, 1763, 1458, 1370, 1350, 1303, 1153 cm.$^{-1}$. Anal. Calcd. for $C_{12}H_{21}NO_4$: C, 59.24; H, 8.70; N, 5.76. Found: C, 59.47; H, 8.91; N, 5.51.

(3R,4S)-1-tert-Butoxycarbonyl-4-cyclohexylmethyl-3-hydroxy-2-azetidinone (6j): 100%; white solid; mp 105–106° C.; $[\alpha]D^{20}$ +61.89° (c 0.74, $CHCl_3$); $^1H$ NMR (300 MHz, $CDCl_3$) δ 0.82–1.84 (m, 13H), 1.50 (s, 9H), 3.82 (bs, 1H), 4.14 (m, 1H), 4.93 (d, J=5.8 Hz, 1H); $^{13}C$ NMR (75 MHz, $CDCl_3$) δ 26.12, 26.17, 26.42, 33.20, 33.47, 33.59, 34.71, 28.00, 57.13, 75.49, 83.47, 148.08, 167.57; IR (KBr) 3442, 2921, 2850, 1797, 1682, 1447, 1354, 1342, 1159 cm$^{-1}$. Anal. Calcd. for $C_{15}H_{25}NO_4$: C, 63.58; H, 8.89; N, 4.94. Found: C, 63.76; H, 8.72; N, 4.68.

(3R,4S)-3-hydroxy-4-phenyl-1-phenylcarbamoyl-2-azetidinone (8a): 88%; white solid; mp 197–200° C.; $[\alpha]D^{20}$ +206.4° (c 1.26, $CHCl_3$); $^1H$ NMR (250 MHz, $CD_3COCD_3$) δ 5.39–5.47 (m, 2H), 7.07–7.60 (m, 10H), 8.80 (bs, 1H); $^{13}C$ NMR (63 MHz, $CD_3COCD_3$) δ 61.98, 78.06, 119.85, 124.31, 128.11, 128.31, 128.60, 129.48, 135.31, 138.43, 148.17, 169.76; IR ($CHCl_3$) 3343, 3018, 2975, 1772, 1712, 1603, 1548, 1447, 1362, 1219, 1045 cm$^{-1}$; MS (FAB) m/z(%) 283(2), 263 (33) 207(22), 143(100).

(3R, 4S)-1-tert-Butylcarbamoyl-3-hydroxy-4-phenyl-2-azetidinone (8b): 89%; white solid; mp 148–151° C.; $[\alpha]D^{20}$ +160.9° (c 1.28, $CHCl_3$); $^1H$ NMR (250 MHz, $CDCl_3$) δ 1.35 (s, 9H), 3.16 (bs, 1H), 4.97 (d, J=5.5 Hz, 1H), 5.11 (d, J=5.5 Hz, 1H), 6.60 (bs, 1H), 7.19–7.38 (m, 5H); $^{13}C$ NMR (63 MHz, $CDCl_3$) δ 28.84, 51.53, 60.74, 76.61, 127.00, 128.61, 128.70, 133.13, 148.78, 168.30; IR ($CHCl_3$) 3362, 3018, 2975, 1767, 1710, 1533, 1422, 1318, 1216, 1045 cm$^{-1}$. Anal. Calcd for $C_{14}H_{18}N_2O_3$: C, 64.11; H, 6.92; N, 10.68. Found: C, 64.10; H, 7.08; N, 10.49.

(3R, 4S)-1-Benzylcarbamoyl-3-hydroxy-4-phenyl-2-azetidinone (8c): 63%; white solid; mp 165–168° C.; $[\alpha]D^{20}$ +139° (c 0.64, $CHCl_3$); $^1H$ NMR (300 MHz, $CDCl_3$) δ3.10 (bs,1H), 4.43 (dd, J=15.2, 5.8 Hz, 1H), 4.50 (dd, J=15.2, 5.8 Hz, 1H), 5.03 (d, J=5.6 Hz, 1H), 5.20 (d, J=5.6 Hz, 1H), 7.06

(t, J=5.8 Hz, 1H), 7.23–7.33 (m, 10H); $^{13}$C NMR (63 MHz, CDCl$_3$) δ 43.79, 61.01, 76.94, 127.13, 127.73, 128.80, 128.86, 132.94, 137.59, 150.15, 168.34; IR (CHCl$_3$) 3364, 3028, 2925, 1771, 1704, 1537, 1455, 1361, 1219, 1190, 987 cm$^{-1}$. Anal. Calcd for C$_7$H$_{16}$N$_2$O$_3$: C$_1$ 68.91; H, 5.44; N. 9.45. Found: C$_1$ 68.89; H. 5.66; N, 9.34.

(3R,4S)-1-Ethylcarbamoyl-3-hydroxy-4-phenyl-2-azetidinone (8d): 55%; white solid; mp 141–42° C.; [α]D$^{20}$ +211.4° (c 0.44, CHCl$_3$); $^1$H NMR (250 MHz, CDCl$_3$) δ 1.19 (t, J=7.2 Hz, 3H), 3.34 (qd, J=7.2, 1.6 Hz, 2H), 5.09 (d, J=5.6 Hz, 1H), 5.27 (d, J=5.6 Hz, 1H), 6.63 (bt, J=1.6 Hz, 1H), 7.23–7.44 (m, 5H); $^{13}$C NMR (63 MHz, CDCl$_3$) δ 15.04, 34.94, 60.77, 76.98, 127.00, 128.92, 129.06, 132.83, 149.96, 167.98; IR (CHCl$_3$) 3381, 3018, 2990, 1770, 1732, 1651, 1589, 1422, 1298, 1210, 1045 cm$^{-1}$.

(3R, 4S)-3-(1-Hydroxy)-1-phenylthiocarbamoyl-4-phenyl-2-azetidinone (8e): 78%; yellow solid; mp 85–88° C.; [α]D$^{20}$ +156.7° (c 0.67, CHCl$_3$); $^1$H NMR (300 MHz, CDCl$_3$) δ 5.16 (d, J=5.8 Hz, 1H), 5.53 (d, J=5.8 Hz, 1H), 7.31–7.44 (m, 8H), 7.66 (d, J=7.8 Hz, 2H), 10.33 (bs, 1H); $^{13}$C NMR (63 MHz, CDCl$_3$) δ 63.97, 75.72, 123.29, 126.49, 127.27, 128.77, 132.49, 137.26, 174.87; IR (CHCl$_3$) 3553, 3295, 3048, 2949, 1760, 1601, 1384, 1313 cm$^{-31\ 1}$; MS (FAB) m/z (%) 299(M+1, 46), 179(100).

(3R,4S)-1-(Morpholinecarbonyl)-3-hydroxy-4-phenyl-2-azetidinone (8f): 83%; white solid; mp 55–57° C.; $^1$H NMR (250 MHz, CDCl$_3$) δ 3.05 (bs, 1H), 3.56–3.78 (m, 8H), 5.00 (d, J=5.9 Hz, 1H), 5.38 (d, J=5.9 Hz, 1H), 7.24–7.40 (m, 5H).

(3R,4S)-1-(N,N-Dimethylcarbamoyl)-3-hydoxy-4-phenyl-2-azetidinone (8g): 88%; white crystal; mp 123–125° C.; $^1$H NMR (250 MHz, CDCl$_3$) δ 3.06 (bs, 6H, 4.98 (d, J=5.9 Hz, 1H), 5.35 (d, J=5.9 Hz, 1H), 7.29–7.39 (m, 5H).

(3R, 4S)-1-tert-Butoxycarbonyl-4-phenyl-3-(1,1,1-trichloroethoxycarbonyloxy)-2-azetidinone (9a): To a solution of 99 mg (0.38 mmol) of 1-tert-butylcarbonyl-3-hydroxy-4-phenyl-2-azetidinone, 5 mg of DMAP and 263 mL (2 mmol) of triethylamine in 5 mL of dichloromethane, was added at 0° C. 105 mL (0.8 mmol) of 1,1,1-trichloroethyl-chloroformate. The reaction mixture was stirred overnight at room temperature. The organic layer was washed several times with brine, dried over MgSO$_4$ and concentrated. The crude solid was purified by chromatography on silica gel to yield 65 mg (40%) of O-protected β-lactam: White solid; mp 122–124° C.; [α]D$^{20}$ +28° (c 0.5, CHCl$_3$); $^1$H NMR (250 MHz, CDCl$_3$) δ 1.39 (s, 9H), 4.43 (d, J=11.7 Hz, 1H), 4.55 (d, J=11.7 Hz, 1H), 5.28 (d, J=5.5 Hz, 1H), 5.76 (d, J=5.5 Hz, 1H), 7.30 (m, 5H); $^{13}$C NMR (63 MHz, CDCl$_3$) δ 27.81, 60.80, 77.03, 78.76, 84.40, 127.73, 128.58, 129.09, 131.55, 147.71, 152.17, 160.34; IR (CHCl$_3$) 3016, 2976, 1819, 1771, 1732, 1683, 1244 cm$^{-1}$. Anal. Calcd for C$_{17}$H$_{18}$Cl$_3$NO$_6$: C, 46.54; H, 4.14; N, 3.19. Found: C, 46.33; H, 4.34; N, 3.33.

(3R,4S)-3-Acetoxy-1-tert-butoxycarbonyl-4-phenyl-2-azetidinone (9b): To a solution of 82 mg (0.3 mmol) of 1-tert-butylcarbonyl-3-hydroxy-4-phenyl-2-azetidinone, 5 mg of DMAP and 210 mL (1.5 mmol) of triethylamine in 5 mL of dichloromethane, was added at 0° C. 58 mL (0.7 mmol) of acetic anhydride. The reaction mixture was stirred overnight at room temperature. The organic layer was washed several times with brine, dried over MgSO$_4$ and concentrated. The crude solid was purified by chromatography on silica gel to yield 71 mg (75%) of O-acetyl β-lactam: White solid; mp 63–64° C.; [α]D$^{20}$ +32.10 (c 0.81, CHCl$_3$); $^1$H NMR (250 MHz, CDCl$_3$) δ 1.37 (s, 9H), 1.65 (s, 3H), 5.22 (d, J=5.5 Hz, 1H), 5.83 (d, J=5.5 Hz, 1H), 7.23–7.33 (m, 5H). $^{13}$C NMR (63 MHz, CDCl$_3$) δ 19.71, 27.81, 60.84, 75.94, 84.07, 127.43, 128.31, 128.67, 132.44, 147.25, 162.39, 168.83; IR (CHCl$_3$) 3026, 2984, 1815, 1752, 1731, 1497, 1371, 1286, 1224, 1152, 1024 cm$^{-1}$. Anal. Calcd for C$_{16}$H$_{19}$NO$_5$: C, 62.94; H, 6.27; N, 4.59. Found: C, 63.17; H, 6.14; N, 4.52.

EXAMPLE 54

To a suspension of NaH (35 mg in 1.0 ML of DME), was added at –10° C., a solution of 133 mg (0.15 mmol) of 7,10-ditroc-10-deacetylbaccatin III and 100 mg (0.30 mmol) of Sd in 1.5 mL of DME. The reaction was monitored by TLC and quenched at –8° C. by addition of brine. The aqueous layer was extracted with dichloromethane. The combined organic layers were washed with brine, dried over Na$_2$CO$_3$ and concentrated. The crude oil was purified by chromatography on silica gel using AcOEt/hexanes (1/2) as the eluant to give 148 mg of the coupling product 2'-EE-7,10-ditroc-Taxotère as a white solid (81% yield; 90% conversion yield) and 12 mg of 7,10-ditroc-10-deacetylbaccatin III (10% recovery).

The EE protecting group was removed by stirring at room temperature 90 mg of 2'-EE-7,10-ditroc-Taxotere in 3 mL of THF and 2 mL of 0.5N HCl for 1 hr. The reaction mixture was diluted with dichloromethane. The organic phase was washed with sat. NaHCO$_3$ sol., brine dried over MgSO$_4$ and concentrated. The crude oil was purified by chromatography on silica gel using AcOEt/hexanes (1/2) as the eluant to give 60 mg (71%) of 2'-OH-7,10-ditroc-Taxotère as a white solid: Mp 154–155° C.; [α]D$^{20\ -38°}$ (c 0.74, CHCl$_3$); $^1$H NMR (250 MHz, CDCl$_3$) δ 1.19 (s, 3H), 1.26 (s, 3H), 1.35 (s, 9H), 1.85 (s, 3H), 1.95 (s, 3H), 2.04 (m, 1H), 2.34 (m, 2H), 2.39 (s, 3H), 2.62 (m, 1H), 3.90 (d, J=6.4 Hz, 1H), 4.17 (d, J=8.4 Hz, 1H), 4.32 (d, J=8.4 Hz, 1H), 4.60 (d, J=11.9 Hz, 1H), 4.64 (m, 1H), 4.78 (s, 2H), 4.91 (d, J=11.9 Hz, 1H), 4.95 (m, 1H), 5.26 (bd, J=8.7 Hz, 1H), 5.46 (bd, J=9.2 Hz, 1H), 5.54 (dd, J=10.4, 7.1 Hz, 1H), 5.69 (d, J=6.8 Hz, 1H), 6.21 (bt, J=8.7 Hz, 1H), 6.24 (s, 1H), 7.32–7.35 (m, 5H), 7.50 (t, J=7.5 Hz, 2H), 7.62 (t, J=7.3 Hz, 1H), 8.10 (d, J=7.5 Hz, 2H); $^{13}$C NMR (63 MHz, CDCl$_3$) δ 10.69, 14.63, 20.91, 22.47, 26.25, 28.14, 33.20, 35.21, 43.07, 46.91, 56.14, 72.17, 73.50, 74.10, 76.48, 77.33, 77.51, 78.55, 79.08, 80.23, 80.67, 83.61, 94.11, 126.70, 128.06, 128.70, 128.88, 130.12, 131.91, 133.79, 138.20, 142.48, 153.12, 153.17, 155.36, 166.82, 170.33, 172.78, 200.70; IR (CHCl$_3$) 3572, 3444, 3034, 2979, 1759, 1737, 1724, 1490, 1450, 1376, 1106 cm$^{-1}$

EXAMPLE 55

To a solution of 90 mg (0.1 mmol) of 7,10-ditroc-10-deacetylbaccatin III and 47 mg (0.14 mmol) of 5d in 5 mL of THF, was added at –30° C. 110 mL (0.11 mmol, 1M in THF) of sodium hexamethyldisilazide. The reaction was monitored by TLC and quenched by addition of brine. The aqueous layer was extracted with dichloromethane. The combined organic layers were washed with brine, dried over Na$_2$CO$_3$ and concentrated. The crude oil was purified by chromatography on silica gel using AcOEt/hexanes (1/2) as the eluant to give 117 mg of the coupling product 2'-EE-7,10-ditroc-Taxotere as a white solid (94%). All physical and spectral data are identical with those of 2'-EE-7,10-ditroc-Taxotere described in Example 54.

The Troc protecting group was removed by stirring at 60° C. 50 mg of 7,10-ditroc-Taxotère in 1 mL of MeOH and 1 mL of AcOH in presence of 150 mg of zinc for 1 hr. The reaction mixture was filtrated and diluted with dichloromethane. The organic phase was washed with sat.

NaHCO₃ sol., brine dried over MgSO₄ and concentrated. The crude oil was purified by chromatography on silica gel using AcOEt/hexanes (1/1) as the eluant to give 28 mg (80%) of Taxotère as a white solid: $[\alpha]D^{20}$ $^{-34°}$ (c 0.7, EtOH); ¹H NMR (250 MHz, CDCl₃) δ 1.13 (s, 3H), 1.26 (s, 3H), 1.35 (s, 9H), 1.80 (s, 3H), 1.85 (m, 1H), 1.90 (s, 3H), 2.24 (m, 2H), 2.39 (s, 3H), 2.55 (m, 1H), 2.62 (m, 1H), 3.53 (s, 1H), 3.92 (d, J=7.0 Hz, 1H), 4.18 (d, J=8.4 Hz, 1H), 4.22 (m, 1H), 4.32 (d, J=8.4 Hz, 1H), 4.66 (d, J=6.9 Hz, 1H), 6.19 (bt, J=8.1 Hz, 1H), 7.32–7.35 (m, 5H), 7.50 (t, J=7.5 Hz, 2H), 7.62 (t, J=7.3 Hz, 1H), 8.10 (d, J=7.5 Hz, 2H). These data are consistent with those reported for Taxotère by Mangatal, L. et al. (Ref. Mangatal, L.; Adeline, M. T.; Guénard, D.; Guéritte-Voegelein, F.; Potier, P. *Tetrahedron* 1989, 45, 4177.)

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What is claimed is:

1. A β-lactam of the formula I:

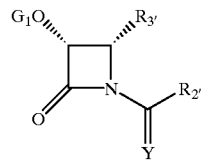

(I)

in which:

R₂' represents RO—, RS—, or RR'N— in which R represents a cycloalkyl, cycloalkenyl, or unsaturated or saturated heterocyclic radical containing 3 to 15 carbon atoms, wherein said heterocyclic radical contains at least one oxygen, nitrogen, or sulfur atom. R' is hydrogen or R as defined above, or R and R' are together an alkylene, alkenylene, or alkynylene of 2 to 10 carbons;

R₃' represents a straight-chain or branched alkyl, alkenyl, or alkynyl radical, or a cycloalkyl, cycloalkenyl, or aryl radical; wherein R and R₃' are unsubstituted or substituted with one or more halogen, hydroxyl, alkoxy, aryloxy, heteroaryloxy, amino, alkylamino, dialkylamino, mercapto, alkylthio, arylthio, heteroarylthio, cyano, carboxyl, alkoxycarbonyl, wherein the alkyl portion contains 1 to 15 carbon atoms, aryloxycarbonyl, wherein the aryl portion contains 6 to 20 carbon atoms, or heteroaryloxycarbonyl radicals, wherein the heteroaryl portion contains 3 to 15 carbon atoms;

G₁ represents a hydrogen or a hydroxyl protecting group; and

Y is oxygen.

2. A β-lactam of the formula I:

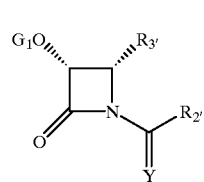

(I)

in which:

R₂' represents RO—, RS—, or RR'N— in which R represents a straight-chain or branched alkyl, alkenyl, or alkynyl radical, a cycloalkyl, cycloalkenyl, aryl, or unsaturated or saturated heterocyclic radical containing 3 to 15 carbon atoms, wherein said heterocyclic radical contains at least one oxygen, nitrogen, or sulfur atom, R' is hydrogen or R as defined above, or R and R' are together an alkylene, alkenylene, or alkynylene of 2 to 10 carbons;

R₃' represents a cycloalkyl or cycloalkenyl radical;

wherein R and R₃' are unsubstituted or substituted with one or more halogen, hydroxyl, alkoxy, aryloxy, heteroaryloxy, amino, alkylamino, dialkylamino, mercapto, alkylthio, arylthio, heteroarylthio, cyano, carboxyl, alkoxycarbonyl, wherein the alkyl portion contains 1 to 15 carbon atoms, aryloxycarbonyl, wherein the aryl portion contains 6 to 20 carbon atoms, or heteroaryloxycarbonyl radicals, wherein the heteroaryl portion contains 3 to 15 carbon atoms;

G₁ represents a hydrogen or a hydroxyl protecting group; and

Y is oxygen.

3. A β-lactam of the formula I:

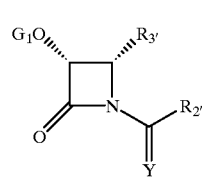

(I)

in which:

R₂' represents RO—, RS—, or RR'N— in which R represents a straight-chain or branched alkyl, alkenyl, or alkynyl radical, a cycloalkyl, cycloalkenyl, aryl, or unsaturated or saturated heterocyclic radical containing 3 to 15 carbon atoms, wherein said heterocyclic radical contains at least one oxygen, nitrogen, or sulfur atom, R' is hydrogen or R as defined above, or R and R' are together an alkylene, alkenylene, or alkynylene of 2 to 10 carbons;

R₃' represents a straight-chain or branched alkyl, alkenyl, or alkynyl radical, or a cycloalkyl, cycloalkenyl, or aryl radical;

wherein R and R₃' are unsubstituted or substituted with one or more halogen, hydroxyl, alkoxy, aryloxy, heteroaryloxy, amino, alkylamino, dialkylamino, mercapto, alkylthio, arylthio, heteroarylthio, cyano, carboxyl, alkoxycarbonyl, wherein the alkyl portion contains 1 to 15 carbon atoms, aryloxycarbonyl, wherein the aryl portion contains 6 to 20 carbon atoms, or heteroaryloxycarbonyl radicals, wherein the heteroaryl portion contains 3 to 15 carbon atoms;

G$_1$ represents a hydrogen or a hydroxyl protecting group; and

Y is sulfur.

4. The β-lactam according to claim 1, 2, or 3 in which R$_2$, represents RO—, RS—, or RR'N—, wherein when R is:
   an alkyl radical, it contains 1 to 10 carbon atoms;
   an alkenyl radical, it contains 2 to 10 carbon atoms;
   an alkynyl radical, it contains 2 to 10 carbon atoms;
   a cycloalkyl radical, it contains 3 to 10 carbon atoms;
   a cycloalkenyl radical, it contains 3 to 10 carbon atoms;
   a heterocyclic radical, it contains 3 to 10 carbon atoms;
   a polycycloalkyl radical, it contains 6 to 20 carbon atoms;
   an aryl radical, it contains 6 to 20 carbon atoms or a heterocyclic aromatic radical, it contains 3 to 15 carbon atoms;

and R' is hydrogen or R as defined above;

and when R$_{31}$ represents:
   an alkyl radical, it contains 1 to 10 carbon atoms;
   an alkenyl radical, it contains 2 to 10 carbon atoms;
   an alkynyl radical, it contains 2 to 10 carbon atoms;
   a cycloalkyl radical, it contains 3 to 10 carbon atoms;
   a cycloalkenyl radical, it contains 3 to 10 carbon atoms; or
   an aryl radical, it contains 6 to 20 carbon atoms.

5. The β-lactam according to claim 2 or 3 in which R$_{2'}$ represents RO—, RS—, RR'N—, wherein R is:
   an alkyl radical selected from methyl, ethyl, propyl, isopropyl, butyl, isobutyl, tert-butyl, pentyl, isopentyl, neopentyl, hexyl, 2-methylpentyl, heptyl, 2-methylhexyl, octyl, and 2-methylheptyl;
   a cycloalkyl radical selected from cyclopropyl, cyclobutyl, cyclopentyl, cylcohexyl, cycloheptyl, adamantyl, and cyclooctyl;
   an alkenyl radical selected from vinyl and allyl;
   an aryl radical selected from phenyl and naphthyl;
   a heterocyclic aromatic radical selected from furyl, pyrrolyl, and pyridyl;
   a cycloalkenyl radical selected from cyclohexenyl, and cycloheptenyl;
   a 9-fluoroenylmethyl radical;
   a benzyl radical;
   a saturated heterocyclic radical selected from oxiranyl, tetrahydrofuryl, prrolidinyl, piperidinyl, tertrahydropyranyl; or
   an unsaturated heterocyclic radical selected from dihydrofuryl, dihydropyrrolyl, dihydropyranyl, or dihydropyrridyl;

R' is hydrogen or R as defined above, and the cyclic RR'N— radical is selected from aziridino, azetidino, pyrrolidino, piperidino, and morpholino.

6. The β-lactam according to claim 1 or 3 in which R$_{3'}$ is:
   an alkyl radical selected from methyl, ethyl, propyl, isopropyl, butyl, isobutyl, tert-butyl, pentyl, isopentyl, neopentyl, hexyl, 2-methylpentyl, heptyl, 2-methylhexyl, octyl, and 2-methylheptyl;
   a 9-fluoroenylmethyl radical;
   a cyclohexylmethyl radical, a cyclohexylethyl radical, a benzyl radical, a tolyl radical, a 2-phenylethenyl, or a phenylethyl radical;
   a cycloalkenyl radical selected from cyclopropyl, cyclobutyl cyclohexyl, cycloheptyl, adamantyl, and cyclootyl;
   an alkenyl radical selected from vinyl and allyl;
   an alkynyl radical selected from ethynyl and propargyl;
   an aryl radical selected from phenyl and naphthyl; or
   a cycloalkenyl radicalselected from cyclohexenyl and cyloheptenyl.

7. The β-lactam according to claim 1, 2, or 3 in which G$_1$ represents a methoxymethyl, methoxyethyl, 1-ethoxyethyl, benzyloxymethyl, (β-trimethylsilyl-ethoxyl)methyl, tetrahydropyranyl, 2,2,2-trichloro-ethoxycarbonyl, benzyloxycarbonyl, tert-butoxycarbonyl, 9-fluorenylmethoxycarbonyl, 2,2,2-trichloroethoxymethyl, trimethylsilyl, triethylsilyl, tripropylsilyl, dimethylethylsilyl, dimethyl(t-butyl)silyl, diethylmethylsilyl, dimethylphenylsilyl, diphenylmethylsilyl, acetyl, chloroacetyl, dichloroacetyl, trichloroacetyl, or trifluoroacetyl group.

8. The β-lactam according to claim 1 wherein R is substituted and the substituents are one or more halogen, hydroxyl, alkoxy, aryloxy, heteroaryloxy, amino, alkylamino, dialkylamino, mercapto, alkylthio, arylthio, heteroarylthio, cyano, carboxyl, alkoxycarbonyl, aryloxycarbonyl, or heteroaryloxycarbonyl radicals.

9. The β-lactam according to claim 2 wherein R is substituted and the substituents are one or more halogen, hydroxyl, alkoxy, aryloxy, heteroaryloxy, amino, alkylamino, dialkylamino, mercapto, alkylthio, arylthio, heteroarylthio, cyano, carboxyl, alkoxycarbonyl, aryloxycarbonyl, or heteroaryloxycarbonyl radicals.

10. The β-lactam according to claim 3 wherein R is substituted and the substituents are one or more halogen, hydroxyl, alkoxy, aryloxy, heteroaryloxy, amino, alkylamino, dialkylamino, mercapto, alkylthio, arylthio, heteroarylthio, cyano, carboxyl, alkoxycarbonyl, aryloxycarbonyl, or heteroaryloxycarbonyl radicals.

11. The β-lactam according to claim 8 wherein the alkyl portion of the alkoxycarbonyl radical contains 1 to 15 carbon atoms and the aryl portion of the aryloxycarbonyl radical contains 6 to 20 carbon atoms.

12. The β-lactam according to claim 9 wherein the alkyl portion of the alkoxycarbonyl radical contains 1 to 15 carbon atoms and the aryl portion of the aryloxycarbonyl radical contains 6 to 20 carbon atoms.

13. The β-lactam according to claim 10 wherein the alkyl portion of the alkoxycarbonyl radical contains 1 to 15 carbon atoms and the aryl portion of the aryloxycarbonyl radical contains 6 to 20 carbon atoms.

* * * * *

UNITED STATES PATENT AND TRADEMARK OFFICE
CERTIFICATE OF CORRECTION

PATENT NO. : 6,187,916 B1  
DATED : February 13, 2001  
INVENTOR(S) : Iwao Ojima Page 1 of 1

It is certified that error appears in the above-identified patent and that said Letters Patent is hereby corrected as shown below:

ABSTRACT,
Column 2,
Line 20, change

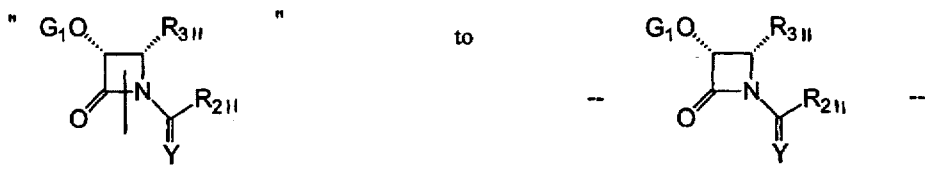

Column 27, claim 1,
Line 48, "atom." should read -- atom, --.

Column 30, claim 6,
Line 14, "radicalselected" should read -- radical selected --.

Signed and Sealed this

Fifth Day of February, 2002

Attest:

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,187,916 B1
DATED : February 13, 2001
INVENTOR(S) : Iwao Ojima

It is certified that error appears in the above-identified patent and that said Letters Patent is hereby corrected as shown below:

<u>Column 1,</u>
Line 16, after "process.", insert -- This work was partially supported by a research grant from the U.S. National Insitutes of Health (GM042798). --.

Signed and Sealed this

Fourth Day of April, 2006

JON W. DUDAS
*Director of the United States Patent and Trademark Office*